United States Patent
Cao et al.

(10) Patent No.: US 11,104,730 B2
(45) Date of Patent: *Aug. 31, 2021

(54) METHODS OF TREATING EYE DISORDERS WITH APLNR ANTAGONISTS AND VEGF INHIBITORS

(71) Applicant: Regeneron Pharmaceuticals, Inc., Tarrytown, NY (US)

(72) Inventors: Jingtai Cao, White Plains, NY (US); Eunice Cheung, Tarrytown, NY (US); Ivan B. Lobov, New York, NY (US)

(73) Assignee: Regeneren Pharmaceuticals, Inc., Tarrytown, NY (US)

(*) Notice: Subject to any disclaimer, the term of this patent is extended or adjusted under 35 U.S.C. 154(b) by 237 days.

This patent is subject to a terminal disclaimer.

(21) Appl. No.: 15/972,053

(22) Filed: May 4, 2018

(65) Prior Publication Data
US 2018/0251545 A1  Sep. 6, 2018

Related U.S. Application Data

(60) Continuation-in-part of application No. 15/480,199, filed on Apr. 5, 2017, now Pat. No. 10,189,901, which is a division of application No. 14/717,914, filed on May 20, 2015, now Pat. No. 9,644,018, which is a continuation-in-part of application No. PCT/US2014/066687, filed on Nov. 20, 2014.

(60) Provisional application No. 62/502,621, filed on May 6, 2017, provisional application No. 61/906,568, filed on Nov. 20, 2013.

(51) Int. Cl.
| | |
|---|---|
| A61K 39/395 | (2006.01) |
| A61P 27/02 | (2006.01) |
| A61K 38/17 | (2006.01) |
| C07K 14/72 | (2006.01) |
| C07K 16/28 | (2006.01) |
| C07K 19/00 | (2006.01) |
| C07K 14/705 | (2006.01) |
| C07K 14/47 | (2006.01) |
| C07K 14/575 | (2006.01) |
| C07K 14/475 | (2006.01) |
| C07K 14/71 | (2006.01) |
| A61K 38/00 | (2006.01) |

(52) U.S. Cl.
CPC .............. *C07K 16/28* (2013.01); *A61K 38/17* (2013.01); *A61K 39/3955* (2013.01); *A61P 27/02* (2018.01); *C07K 14/47* (2013.01); *C07K 14/705* (2013.01); *C07K 14/72* (2013.01); *C07K 16/2869* (2013.01); *C07K 19/00* (2013.01); *A61K 38/00* (2013.01); *C07K 14/475* (2013.01); *C07K 14/575* (2013.01); *C07K 14/71* (2013.01); *C07K 2317/21* (2013.01); *C07K 2317/24* (2013.01); *C07K 2317/56* (2013.01); *C07K 2317/565* (2013.01); *C07K 2317/74* (2013.01); *C07K 2317/76* (2013.01); *C07K 2317/92* (2013.01); *C07K 2319/30* (2013.01)

(58) Field of Classification Search
CPC . C07K 16/28; C07K 16/2869; A61K 39/3955
See application file for complete search history.

(56) References Cited

U.S. PATENT DOCUMENTS

| | | | |
|---|---|---|---|
| 6,833,349 B2 | 12/2004 | Xia et al. | |
| 7,736,646 B2 * | 6/2010 | Krieg ...................... | A61P 7/06 424/133.1 |
| 9,644,018 B2 | 5/2017 | Stevis et al. | |
| 10,155,811 B2 | 12/2018 | Stevis et al. | |
| 10,189,901 B2 | 1/2019 | Stevis et al. | |
| 10,626,173 B2 | 4/2020 | Stevis et al. | |
| 2015/0252107 A1 | 9/2015 | Stevis et al. | |
| 2016/0024483 A1 | 1/2016 | Kim et al. | |
| 2016/0144025 A1 | 5/2016 | Vitti et al. | |
| 2017/0058028 A1 | 3/2017 | Stevis et al. | |
| 2017/0210800 A1 | 7/2017 | Stevis et al. | |
| 2019/0177410 A1 | 6/2019 | Stevis et al. | |

FOREIGN PATENT DOCUMENTS

WO          15/077491 A1      5/2015

OTHER PUBLICATIONS

Frampton, 2012. Drugs Aging. 29: 839-846.*
Benjamini etal, 1991. Immunology: A Short Course, 2nd edition, p. 40 only.*
Ferrara etal (2015. mAbs. 7(1): 32-41).*
ClinicalTrial.org Identifier: NCT02418754, "Study of Intravitreal REGN2176-3 in Patients with Neovascular ("Wet") Age-Related Macular Degeneration (AMD)(Capella)," (2015). [Retrieved from the Internet Sep. 24, 2018: <URL: https:clinicaltrials.gov/ct2/show/NCT02418754>].
Engerman et al., "Perspectives in Diabetes, Pathogenesis of Diabetic Retinopathy," Diabetes, vol. 38:1203-1206, (Oct. 1989).
Kasai et al., "Apelin is a Crucial Factor for Hypoxia-Induced Retinal Angiogenesis," Arterioscler Thromb Vasc Biol, vol. 30:2182-2187, (2010). DOI: 10.1161/ATVBAHA.110.209775 [Retrieved from the Internet May 5, 2017: <URL: http://atvb.ahajournals.org>].
Kasai et al., "Retardation of Retinal Vascular Development in Apelin-Deficient Mice," Arterioscler Throm Vasc Biol, vol. 28:1717-1722, (2008). DOI: 10.1161/ATVBAHA.108.163402 [Retrieved from the Internet May 5, 2017: <URL: http://atvb.ahajournals.org>].

(Continued)

*Primary Examiner* — Zachary C Howard
(74) *Attorney, Agent, or Firm* — Schwabe, Williamson & Wyatt PC; Christopher Westberg

(57) ABSTRACT

The present disclosure provides methods for treating, preventing or reducing the severity of an eye disease. The methods of the present disclosure comprise administering to a subject in need thereof a therapeutic composition comprising an APLNR antagonist such as an anti-APLNR antibody in combination with a vascular endothelial growth factor (VEGF) antagonist (for example, aflibercept).

46 Claims, 23 Drawing Sheets

Specification includes a Sequence Listing.

(56) References Cited

OTHER PUBLICATIONS

Kidoya et al., "The apelin/APJ system induces maturation of the tumor vasculature and improves the efficiency of immune therapy," Oncogene, vol. 31:3254-3264, (2012). DOI: 10.1038/onc.2011.489.

Lu et al., "Apelin in epiretinal membranes of patients with proliferative diabetic retinopathy," Molecular Vision, vol. 20:1122-1131, (2014). [<URL: http://www.molvis.org/molvis/v20/1122>].

Ophthotech Corporation, "Ophthotech Announces Results from Third Phase 3 Trial of Fovista in Wet Age-Related Macular Degeneration," General Release, Aug. 14, 2017.

Qian et al., "Vitreous and Plasma Concentrations of Apelin and Vascular Endothelial Growth Factor After Intravitreal Bevacizumab in Eyes with Proliferative Diabetic Retinopathy," Retina, vol. 31:161-168, (2011).

Zhang et al., "Apelin in Epiretinal Fibrovascular Membranes of Patients with Retinopathy of Prematurity and the Changes After Intravitreal Bevacizumab," Retina, vol. 33:613-620, (2013).

Eleftheriadou et al., "Long-Term Outcomes of Aflibercept Treatment for Neovascular Age-Realted Macular Degeneration in a Clinical Setting," American Journal of Ophthalmology Elsevier, Amsterdam, NL, vol. 174:160-168, (2016); XP029890555, ISSN: 0002-9394, DOI: 10.1016/J.AJO.2016-09-038.

Greenwood et al., "Apelin Is Required for Non-sprouting Vascular Remodeling in the Developing and Pathogenic Retina," ARVO Annual Meeting Abstract Search and Program Planner, vol. 2011: p. 4823 (2011); XP009507405.

Sakimoto et al., "A role of endothelial cells in promoting the maturation of astrocytes through the apelin/APJ system in mice," Development, The Company Biologists LTD, GB, vol. 139 (No. 7):1327-1335, (2012); XP005907404, ISSN: 0950-1991, DOI: 10.1242/DEV.072330.

WIPO Application No. PCT/US2018/031255, PCT International Search Report and Written Opinion of the International Searching Authority dated Aug. 27, 2018.

U.S. Appl. No. 61/906,568, filed Nov. 20, 2013, Expired.
PCT/US2014/066687, filed Nov. 20, 2014, WO 2015/077491, Expired.
U.S. Appl. No. 14/717,914, filed May 20, 2015, U.S. Pat. No. 9,644,018, Issued.
U.S. Appl. No. 15/480,199, filed Apr. 5, 2017, U.S. Pat. No. 10,189,901, Issued.
U.S. Appl. No. 62/502,621, filed May 6, 2017, Expired.
PCT/US2018/031255, filed May 4, 2018, WO 2018/208625, Expired.
U.S. Appl. No. 15/038,202, filed May 20, 2016, U.S. Pat. No. 10,155,811, Issued.
U.S. Appl. No. 16/175,357, filed Oct. 20, 2018, U.S. Pat. No. 10,626,173, Issued.
U.S. Appl. No. 16/218,862, filed Dec. 13, 2018, U.S. Pat. No. 2019-0177410, Published.

* cited by examiner

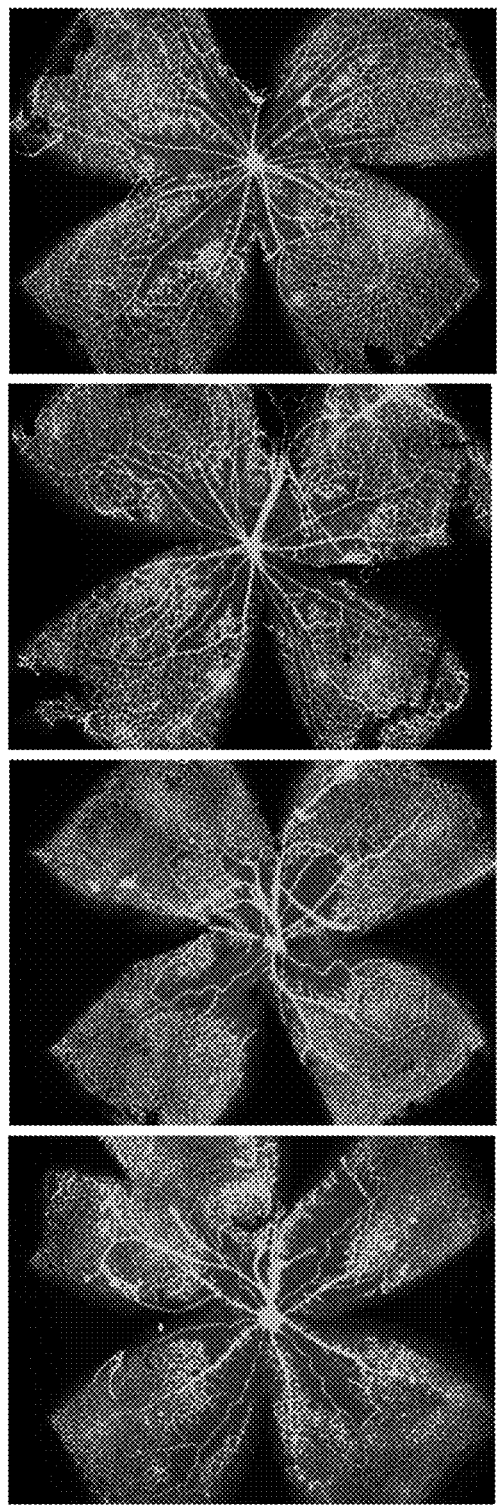

METHODS OF TREATING EYE DISORDERS WITH APLNR ANTAGONISTS AND VEGF INHIBITORS

CROSS-REFERENCE TO RELATED APPLICATIONS

This application claims the benefit under 35 USC § 119(e) of U.S. Provisional Application No. 62/502,621, filed May 6, 2017. This application is also a continuation-in-part of U.S. application Ser. No. 15/480,199, filed Apr. 5, 2017, which is a division of U.S. application Ser. No. 14/717,914, filed May 20, 2015, which is a continuation-in-part of International Application No. PCT/US2014/066687, filed Nov. 20, 2014, which claims the benefit under 35 USC § 119(e) of U.S. Provisional Application No. 61/906,568, filed Nov. 20, 2013. Each of these applications is incorporated herein by reference in its entirety for all purposes.

SEQUENCE LISTING

This application incorporates by reference the Sequence Listing submitted in Computer Readable Form as file 10354US01-Sequence.txt, created on May 4, 2018 and containing 17,010 bytes.

FIELD OF THE DISCLOSURE

The present disclosure relates to methods of treating vascular eye disease, in particular, by administering an apelin receptor antagonist and a vascular endothelial growth factor (VEGF) antagonist to a subject in need thereof.

BACKGROUND

Vascular eye diseases are the leading cause of vision loss in today's aging population. These diseases may be characterized by abnormal 'leaky' blood vessels growing into the retina. Two of the largest contributors to this subject population are diabetic retinopathy and exudative age-related macular degeneration.

Diabetic retinopathy (DR) is a major cause of visual impairment in the United States (Klein et al., 1984, Ophthalmology 91:1464-1474; Moss et al., 1998, Ophthalmology 105:998-1003). Diabetic retinopathy results from microvascular decompensation beginning with basement membrane thickening (Ruggiero et al., 1997, Diabetes Metab. 23:30-42), and eventually leading to vascular occlusion and neovascularization (Porta et al., 2002, Diabetologia 45:1617-1634). It is estimated that about 28% of subjects 40 years and older with diabetes have DR, and 4.4% have vision threatening DR (Zhang et al., 2010, JAMA 304: 649-656). Diabetic macular edema (DME) is a manifestation of DR and is the most frequent cause of blindness in young and mid-aged adults (Klein et al., 1984, Ophthalmology 91:1464-1474; Moss et al., 1998, Ophthalmology 105:998-1003).

Age-related macular degeneration (AMD) is the leading cause of severe visual loss in people aged 50 years or older in the developed world. In recent years, major advances have been made in the treatment of AMD, with the introduction of anti-angiogenic agents, offering hope of significant visual recovery for subjects with neovascular AMD (Keane et al., 2012, Surv Ophthalmol. 57: 389-414).

Preproapelin is a 77 amino acid protein expressed in the human CNS and peripheral tissues, e.g., lung, heart, and mammary gland. Peptides comprising C-terminal fragments of varying size of apelin peptide were shown to activate the G protein-coupled receptor, APJ receptor (now known as APLNR) (Habata, et al., 1999, Biochem Biophys Acta 1452:25-35; Hosoya, et al., 2000, JBC, 275 (28):21061-67; Lee, et al., 2000, J Neurochem 74:34-41; Medhurst, et al., 2003, J Neurochem 84:1162-1172). Many studies indicate that apelin peptides and analogues convey cardiovascular and angiogenic actions through their interaction with the APJ receptor (APLNR), such as endothelium-dependent vasodilation (Tatemoto et al., 2001, Regul Pept 99:87-92).

The apelin system appears to play a role in pathophysiological angiogenesis. Studies have indicated that apelin may be involved in hypoxia-induced retinal angiogenesis (Kasai et al., 2010, Arterioscler Thromb Vasc Biol 30:2182-2187). In some reports, certain compositions may inhibit angiogenesis by inhibiting the apelin/APJ pathway (see, e.g., U.S. Pat. No. 7,736,646), such as APLNR inhibitors capable of blocking pathological angiogenesis and therefore useful in inhibiting vascularization in the retina (Kojima, Y. and Quertermous, T., 2008, Arterioscler Thromb Vasc Biol 28:1687-1688). As such, interference with apelin-mediated signaling may also be beneficial in early prevention of proliferative diabetic retinopathy (Tao et al., 2010, Invest Opthamol Visual Science 51:4237-4242; Du, J H et al., Int J Ophthalmol. 2014 Dec. 18; 7 (6):968-73; Lu, Q. et al., 2013, PLoS One 8 (7):e69703). More recently, apelin has been implicated in the mechanism of retinopathy of prematurity (Ali Y F et al., Clin Ophthalmol. 2017 Feb. 21; 11:387-392).

Anti-vascular endothelial growth factor (VEGF) therapy (e.g., aflibercept) is standard of care treatment for neovascular AMD and DME. The efficacy and safety of aflibercept in these subject populations is well-characterized (Dixon et al., 2009; Expert Opin. Investig. Drugs 18: 1573-80). However, in AMD, although approximately 95% of subjects maintained their vision, only approximately 30% of subjects achieved an improvement of 15 or more letters in best corrected visual acuity (BCVA) at 1 year. In DME, there is also the possibility of improving treatment outcomes. As seen with aflibercept and with ranibizumab, less than 50% of subjects with vision loss due to DME achieve a 15 or more letter improvement over 1 and 2 years. Also, in the studies with ranibizumab, clinical evidence of proliferative retinopathy developed in up to 7.2% of subjects who had received 3 years of monthly treatment of ranibizumab, with up to 3.2% of subjects requiring panretinal photocoagulation, a potentially visually disabling treatment modality (Brown et al., 2013 Ophthalmology 10: 2013-22).

Although both apelin/APLNR and VEGF are known contributors to angiogenesis and vascular development, the mechanism by which the two signaling pathways interact in the promotion of angiogenesis remains incompletely understood. In particular, these pathways are known to be involved in the formation of retinal vessels, and various studies have reported that apelin and VEGF have positive and negative feedback effects, in which increased expression of one can contribute to the expression of the other, or antagonism of one suppresses the expression of the other (Lu et al., 2014, Molecular Vision, 20:1122-1131).

Intravitreal (IVT) deliveries of anti-VEGF therapies such as ranibizumab and aflibercept have demonstrated efficacy and safety for chorioretinal diseases. However, there are many additional factors that contribute to vascular permeability, neovascularization, and other vascular dysfunction.

BRIEF SUMMARY OF THE DISCLOSURE

In one aspect, the present invention provides methods for treating, preventing or ameliorating at least one symptom or indication of a vascular eye disease or disorder in a subject. The methods include administering a therapeutically effective amount of a pharmaceutical composition comprising an APLNR antagonist to a subject in need thereof. In certain embodiments, the APLNR antagonist is administered in combination with a vascular endothelial growth factor (VEGF) antagonist, for example by administration of a therapeutically effective amount of a pharmaceutical composition comprising a VEGF antagonist.

In certain embodiments, the eye disease or disorder is selected from the group consisting of diabetic retinopathy, diabetic macular edema, age-related macular degeneration, retinal neovascularization, central retinal vein occlusion, branched retinal vein occlusion, polypoidal choroidal vasculopathy, choroidal neovascularization (CNV), degenerative myopia (myopic CNV), neovascular glaucoma, and retinopathy of prematurity.

In another aspect, the present invention provides methods for inhibiting retinal angiogenesis in a subject. The methods comprise administering a therapeutically effective amount of a pharmaceutical composition comprising an APLNR antagonist in combination with a VEGF antagonist to the subject in need thereof. In some embodiments, the retinal angiogenesis is associated with a vascular eye disease or disorder.

In another aspect, the present invention provides methods for inhibiting retinal neovascularization (e.g., in a subject with an eye disease or disorder associated with angiogenesis). The methods comprise administering a therapeutically effective amount of a pharmaceutical composition comprising an APLNR antagonist in combination with a VEGF antagonist to the subject in need thereof.

In another aspect, the present invention provides methods for inhibiting choroidal neovascularization in a subject. The methods comprise administering a therapeutically effective amount of a pharmaceutical composition comprising an APLNR antagonist in combination with a VEGF antagonist to the subject in need thereof.

In another aspect, the present invention provides methods for improving vascular regrowth and decreasing abnormal neovascularizations in a subject. The methods comprise administering a therapeutically effective amount of a pharmaceutical composition comprising an APLNR antagonist in combination with a VEGF antagonist to the subject in need thereof.

In another aspect, the present invention provides methods for promoting revascularization of a retina in a subject in need thereof. The methods comprise administering a therapeutically effective amount of an APLNR antagonist to a subject in need thereof; and administering a therapeutically effective amount of a vascular endothelial growth factor (VEGF) antagonist, to the subject.

In another aspect, the present invention provides methods for promoting uniform regrowth of retinal vessels in a subject in need thereof. The methods comprise administering a therapeutically effective amount of an APLNR antagonist to a subject in need thereof; and administering a therapeutically effective amount of a vascular endothelial growth factor (VEGF) antagonist, to the subject.

In another aspect, the present invention provides methods of improving vessel outgrowth in a retina of a subject in need thereof. The methods comprise administering a therapeutically effective amount of an APLNR antagonist to a subject in need thereof; and administering a therapeutically effective amount of a vascular endothelial growth factor (VEGF) antagonist, to the subject.

In another aspect, the present invention provides methods for promoting uniform blood vessel growth in a retina in a subject in need thereof. The methods comprise administering a therapeutically effective amount of an APLNR antagonist to a subject in need thereof; and administering a therapeutically effective amount of a vascular endothelial growth factor (VEGF) antagonist, to the subject.

In another aspect, the present invention provides methods for improving blood vessel organization of a retina in a subject in need thereof. The methods comprise administering a therapeutically effective amount of an APLNR antagonist to a subject in need thereof; and administering a therapeutically effective amount of a vascular endothelial growth factor (VEGF) antagonist, to the subject.

In any of the methods discussed above or herein, the subject may be an individual that has been diagnosed with an eye disease or disorder. In some cases, the eye disease or disorder is selected from the group consisting of diabetic retinopathy, proliferative diabetic retinopathy, diabetic macular edema, age-related macular degeneration, retinal neovascularization, central retinal vein occlusion, branched retinal vein occlusion, polypoidal choroidal vasculopathy, choroidal neovascularization (CNV), degenerative myopia (myopic CNV), neovascular glaucoma, and retinopathy of prematurity. In some cases, the eye disease or disorder is age-related macular degeneration. In some cases, the eye disease or disorder is diabetic macular edema. In some cases, the eye disease or disorder is retinopathy of prematurity. In some cases, the eye disease or disorder is proliferative diabetic retinopathy.

Exemplary APLNR antagonists that can be used in the context of the methods or compositions of the present disclosure include small molecule chemical inhibitors of APLNR, or biological agents that target APLNR, such as peptides, peptide mimetics and antibodies. In certain embodiments, the APLNR antagonist blocks the interaction of APLNR and apelin.

According to certain embodiments, the APLNR antagonist is an antibody or antigen-binding protein that binds the APLNR antagonist and inhibits APLNR signaling. In certain embodiments, the anti-APLNR antibody or antigen-binding protein comprises the heavy chain complementarity determining regions (HCDRs) of a heavy chain variable region (HCVR) comprising the amino acid sequence of SEQ ID NO: 2 or 13 and the light chain CDRs of a light chain variable region (LCVR) comprising the amino acid sequence of SEQ ID NO: 7 or 18. In certain embodiments, the anti-APLNR antibody or antigen-binding protein comprises the complementarity determining regions (CDRs) of a heavy chain variable region (HCVR) of an anti-APLNR antibody selected from the group consisting of H2aM9232N (or H4H9232N) and H1M9207N.

In any of the methods or compositions discussed above or herein, the APLNR antagonist may comprise an anti-APLNR antibody or antigen-binding fragment thereof, wherein the antibody or antigen-binding fragment thereof specifically binds human APLNR. In some cases, the antibody or antigen-binding fragment thereof competes for binding to human apelin receptor (APLNR) with a reference antibody comprising an HCVR/LCVR sequence pair selected from the group consisting of SEQ ID NOs: 2/7 and 13/18, wherein the antibody or antigen-binding fragment thereof specifically binds human APLNR. In some cases, the antibody or antigen-binding fragment thereof binds to the same epitope on APLNR as a reference antibody comprising an HCVR/LCVR sequence pair selected from the group consisting of SEQ ID NOs: 2/7 and 13/18, wherein the antibody or antigen-binding fragment thereof specifically binds human APLNR. In some cases, the antibody or antigen-binding fragment comprises: (a) the complementarity determining regions (CDRs) of a heavy chain variable region (HCVR) having an amino acid sequence selected from the group consisting of SEQ ID NOs: 2 and 13; and (b) the CDRs of a light chain variable region (LCVR) having an amino acid sequence selected from the group consisting of SEQ ID NOs: 7 and 18. In some cases, the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21. In some cases, the antibody or antigen-binding fragment comprises: (a) a heavy chain variable region (HCVR) having an amino acid sequence selected from the group consisting of SEQ ID NOs: 2 and 13; and (b) a light chain variable region (LCVR) having an amino acid sequence selected from the group consisting of SEQ ID NOs: 7 and 18. In some cases, the antibody or antigen-binding fragment comprises the heavy and light chain CDRs of a HCVR/LCVR amino acid sequence pair selected from the group consisting of: SEQ ID NOs: 2/7 and 13/18. In some cases, the antibody or antigen-binding fragment comprises a HCVR/LCVR amino acid sequence pair selected from the group consisting of: SEQ ID NOs: 2/7 and 13/18.

In one embodiment of any one of the methods or compositions discussed above or herein, the antibody or antigen-binding fragment thereof comprises the HCVR/LCVR amino acid sequence pair of SEQ ID NOs: 2/7.

In one embodiment of any one of the methods or compositions discussed above or herein, the antibody or antigen-binding fragment thereof comprises the HCVR/LCVR amino acid sequence pair of SEQ ID NOs: 13/18.

In any one of the methods or compositions discussed above or herein, the antibody or antigen-binding fragment can be a human antibody with an IgG1 or IgG4 heavy chain constant region. In one embodiment, the heavy chain constant region is human IgG1. In one embodiment, the heavy chain constant region is human IgG4.

In various embodiments of any one or the methods or compositions discussed above or herein, the antibody or antigen-binding fragment thereof blocks the interaction of APLNR and apelin. In some cases, the antibody or antigen-binding fragment thereof blocks the interaction of APLNR and apelin exhibiting at least 50% binding inhibition in a competitive binding assay. In other embodiments, the antibody or antigen-binding fragment thereof does not block, or only partially blocks the interaction of APLNR and apelin.

VEGF antagonists that may be used in combination with an APLNR antagonist in the compositions and methods of the present disclosure include anti-VEGF antibodies (e.g., ranibizumab), small molecule VEGF inhibitors (e.g., sunetinib), and VEGF-inhibiting fusion proteins ("VEGF Traps"). An example of a VEGF antagonist that may be used in combination with the APLNR antagonist in the methods of treatment of the present disclosure is aflibercept, a VEGF-inhibiting fusion protein (see e.g. U.S. Pat. No. 7,087,411).

In any one of the methods or compositions discussed above or herein, the VEGF antagonist comprises a VEGF receptor-based chimeric molecule (VEGF Trap). In some cases, the VEGF Trap comprises one or more immunoglobulin (Ig)-like domains of VEGFR1, one or more Ig-like domains of VEGFR2, and a multimerizing domain. In some cases, the VEGF Trap comprises Ig-like domain 2 of VEGFR1, Ig-like domain 3 of VEGFR2, and a multimerizing domain. In some cases, the VEGF Trap is aflibercept, or a biosimilar molecule thereof. In some cases, the VEGF antagonist consists of a dimer of two polypeptides consisting of amino acids 27-457 of SEQ ID NO: 23.

In another aspect, the present disclosure provides a pharmaceutical composition comprising a therapeutically effective amount of an APLNR antagonist and a pharmaceutically acceptable carrier or diluent. In certain embodiments, the pharmaceutical composition further comprises a VEGF antagonist.

In various embodiments, the present disclosure provides for the use of an APLNR antagonist in conjunction with a VEGF antagonist in the manufacture of a medicament to treat an eye disease or disorder in a subject, including humans, or to perform the other objectives of any of the methods discussed above or herein. All of the methods discussed above or herein can be embodied as a use or uses of the APLNR antagonists and VEGF antagonists for the treatment of eye diseases or disorders or other objectives of the recited methods. Other embodiments include the APLNR antagonists and VEGF antagonists for use in the methods discussed above or herein.

In another aspect, the present invention provides a composition for treating a vascular eye disease or disorder, in which the composition comprises a therapeutically effective amount of an APLNR antagonist, a therapeutically effective amount of a vascular endothelial growth factor (VEGF) antagonist, and a suitable carrier, excipient or diluent. In various embodiments of the composition, the APLNR antagonist or the VEGF antagonist can be as discussed above or herein.

Other embodiments will become apparent from a review of the ensuing detailed description.

BRIEF DESCRIPTION OF THE DRAWINGS

FIGS. 8A and 8B are representative photomicrographs (20×) of OIR mouse retinas treated systemically at P12 to P16 and graphs of the calculated avascular area. The rate of regrowth with the combination treatment is similar to each agent alone, vascular regrowth is improved compared to hFc-treated control retinas, and there were significant changes in avascular area between treatment groups (p<0.0005).

FIG. 9B shows that there were significant changes in abnormal vascular area between treatment groups (p<0.0005). Abnormal vascular area was significantly decreased with anti-APLNR (*, p<0.0005), with aflibercept (* p<0.005), and with the combination (***, p<0.0005) compared to Fc control, and the abnormal vascular area was also significantly decreased in the combination treatment group (*, p<0.05) compared to the anti-APLNR treatment group

As shown in FIG. 11A, the combination of anti-APLNR antibody and aflibercept produced retinal vessels that are more organized and uniform compared to anti-APLNR alone, and less sparse (with fewer pruned vessels) compared to aflibercept alone. FIG. 11B shows that there were significant changes in vessel area between the treatment groups (p<0.0005). Vessel area was significantly increased with anti-APLNR (*, p<0.0005) and decreased with aflibercept (*, p<0.005) and the combination treatment (*, p<0.05) compared to Fc control. Vessel area was significantly decreased with aflibercept (####, p<0.0005) and with the combination (####, p<0.0005) compared to anti-APLNR. In contrast, vessel area was significantly increased with the combination treatment (&&&, p<0.005) compared to aflibercept.

As shown in FIG. 12A, the combination of anti-APLNR antibody and aflibercept produced retinal vessels of intermediate density compared to anti-APLNR (greater density) or aflibercept (lesser density) alone. FIG. 12B shows that there were significant changes in vessel length between the treatment groups (p<0.0005). Vessel length was significantly decreased with aflibercept (####, p<0.0005) and with the combination (####, p<0.0005) compared to anti-APLNR. In contrast, vessel length was significantly increased with the combination treatment (&&&, p<0.005) compared to aflibercept.

DETAILED DESCRIPTION

Figure 1A:
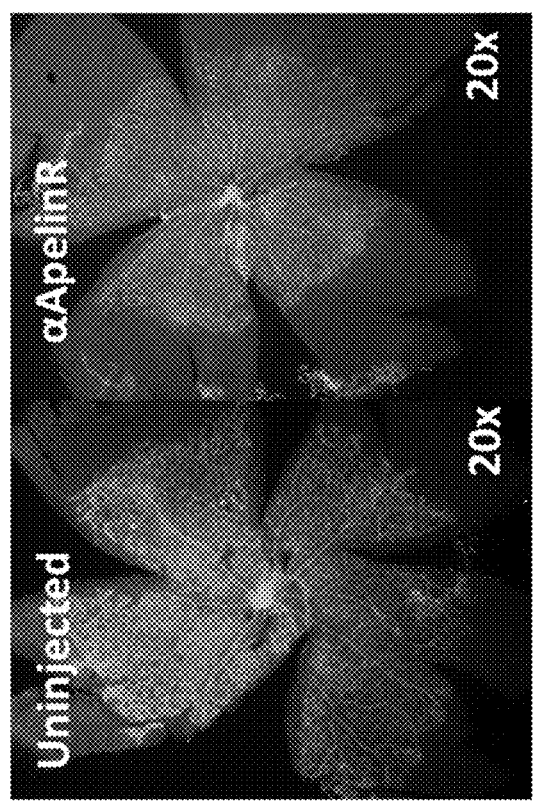
FIGS. 1A and 1B are representative photomicrographs of mouse retinas treated systemically (IP) at P2 to P5 and a graph of the calculated vascular area. Residual vascular area was significantly smaller in αApelinR (anti-APLNR antibody H2aM9232N) treated (23% at 25 mg/kg, $p<0.05$) retinas compared to untreated retinas. Retinal endothelial cells were stained with GS Lectin I. Images were taken at 20× (for quantification) and 40×. Statistical analysis was done with Student T-test. Selective inhibition of ApelinR via systemic injection delayed normal vascular outgrowth in the developing retina in P5 pups. At 25 mg/kg Dose, blocking ApelinR slightly inhibits vascular outgrowth.
Figure 1A:
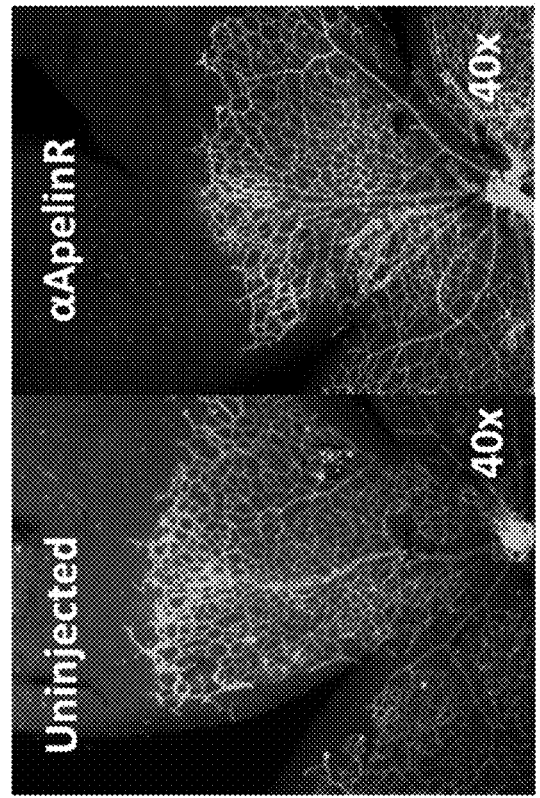

Before the present disclosure is described, it is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present disclosure, the preferred methods and materials are now described. All patents, applications and non-patent publications mentioned in this specification are incorporated herein by reference in their entireties.

The present invention and disclosure is based, in part, on the surprising discovery that the combination of an APLNR antagonist and a VEGF antagonist (e.g., an anti-APLNR antibody and a VEGF Trap) can produce more organized and ordered revascularization of intermediate density (with fewer pruned vessels) in the retina of a subject than is observed with either an APLNR antagonist or a VEGF antagonist, alone.

Definitions

The expressions "apelin receptor," "APLNR," "ApelinR," "APJ receptor," and the like, as used herein, refer to a human APLNR protein having the amino acid sequence set forth as:

(SEQ ID NO: 22)
MEEGGDFDNYYGADNQSECEYTDWKSSGALIPAIYMLVFLLGTTGNGLVL

WTVFRSSREKRRSADIFIASLAVADLTFVVTLPLWATYTYRDYDWPFGTF

FCKLSSYLIFVNMYASVFCLTGLSFDRYLAIVRPVANARLRLRVSGAVAT

AVLWVLAALLAMPVMVLRTTGDLENTTKVACYMDYSMVATVSSEWAWEVG

LGVSSTTVGFVVPFTIMLTCYFFIAQTIAGHFRKERIEGLRKRRRLLSII

VVLVVTFALCWMPYHLVKTLYMLGSLLHWPCDFDLFLMNIFPYCTCISYV

NSCLNPFLYAFFDPRFRQACTSMLCCGQSRCAGTSHSSSGEKSASYSSGH

SQGPGPNMGKGGEQMHEKSIPYSQETLVVD, or a substantially similar amino acid sequence to SEQ ID NO: 22. All references to proteins, polypeptides and protein fragments herein are intended to refer to the human version of the respective protein, polypeptide or protein fragment unless explicitly specified as being from a non-human species (e.g., "mouse APLNR," "monkey APLNR," etc.).

As used herein, "an antibody or antigen-binding fragment that binds APLNR" or an "anti-APLNR antibody" includes immunoglobulin molecules, antibodies and antigen-binding fragments thereof that bind a fragment of an APLNR protein. APLNR molecules include natural APLNR proteins as well as recombinant APLNR protein variants such as, e.g., monomeric and dimeric APLNR constructs. In embodiments, an antibody that binds APLNR or antigen binding fragment thereof is an APLNR antagonist.

The term "antagonist", as used herein, refers, in part, to a moiety that binds to the receptor at the same site or near the same site as an agonist (for example, the endogenous ligand), but which does not activate the intracellular response typically initiated by the active form of the receptor, and thereby inhibits or neutralizes the intracellular response by an agonist or partial agonist. The term antagonist may also refer, in part, to a moiety that binds to a receptor agonist, thereby sequestering the agonist from interaction with its cognate receptor. An example of an antagonist that binds an agonist is a ligand trap, such as a VEGF trap. In some cases, antagonists do not diminish the baseline intracellular response in the absence of an agonist or partial agonist. An antagonist does not necessarily have to function as a competitive binding inhibitor, but may work by sequestering an agonist, or indirectly modulating a downstream effect.

As used herein, the term APLNR antagonist may refer to a moiety that binds to the APLNR receptor at the same site or near the same site as an agonist (for example, apelin), but which does not activate the intracellular response typically initiated by the active form of the receptor, and thereby inhibits or neutralizes the intracellular response of APLNR. In embodiments, an APLNR antagonist is an antibody or antigen binding fragment thereof that binds APLNR. Examples of APLNR antagonists can be found in International Patent Publication No. WO2015077491, published May 28, 2015, which is specifically incorporated herein by reference in its entirety. Other APLNR antagonists can include small molecules and other biological entities, such as peptides.

The term "immunoglobulin" (Ig) refers to a class of structurally related glycoproteins consisting of two pairs of polypeptide chains, one pair of light (L) chains and one pair of heavy (H) chains, which may all four be inter-connected by disulfide bonds. The structure of immunoglobulins has been well characterized. See for instance Fundamental Immunology Ch. 7 (Paul, W., ed., 2nd ed. Raven Press, N.Y. (1989)).

The term "antibody", as used herein, means any antigen-binding molecule or molecular complex comprising at least one complementarity determining region (CDR) that specifically binds to or interacts with a particular antigen (e.g., APLNR). The term "antibody" includes immunoglobulin molecules comprising four polypeptide chains, two heavy (H) chains and two light (L) chains inter-connected by disulfide bonds, as well as multimers thereof (e.g., IgM), as well as immunoglobulin molecules including a fragment of one or more heavy chains or a fragment of one or more light chains, (e.g. Fab, F(ab')$_2$ or scFv fragments), as described herein. Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-APLNR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Such techniques may also be employed to synthesize any antibody-fusion molecule containing an antigen-binding fragment derived from a full antibody molecule.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$, (ii) $V_H$-$C_H2$; (iii) $V_H$-$C_H3$; (iv) $V_H$-$C_H1$-$C_H2$, (v) $V_H$-$C_H1$-CH2-$C_H3$, (vi) $V_H$-$C_H2$-$C_H3$; (vii) $V_H$-$C_L$; (viii) $V_L$-CH1, (ix) $V_L$-$C_H2$; (x) $V_L$-$C_H3$; (xi) $V_L$-CH1-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

The phrase "antibody-fusion proteins" includes recombinant polypeptides and proteins derived from antibodies of the disclosure that have been engineered to contain an antibody or antigen-binding fragment as described herein. The peptide component may be fused to the anti-APLNR antibody or antigen-binding fragment either at the N-terminus or the C-terminus of the antibody light chain or heavy chain, with or without peptide linkers. The phrase "fused to", as used herein, means (but is not limited to) a polypeptide formed by expression of a chimeric gene made by combining more than one sequence, typically by cloning one gene into an expression vector in frame with a second gene such that the two genes are encoding one continuous polypeptide. Recombinant cloning techniques, such as polymerase chain reaction (PCR) and restriction endonuclease cloning, are well-known in the art. In addition to being made by recombinant technology, parts of a polypeptide can be "fused to" each other by means of chemical reaction, or other means known in the art for making custom polypeptides.

In some embodiments, the components or amino acids of an antibody-fusion protein are separated by a linker (or "spacer") peptide. Such peptide linkers are well known in the art (e.g., polyglycine or Gly-Ser linkers) and typically allow for proper folding of one or both of the components of the antibody-fusion protein. The linker provides a flexible junction region of the component of the fusion protein, allowing the two ends of the molecule to move independently, and may play an important role in retaining each of the two moieties' appropriate functions. Therefore, the junction region acts in some cases as both a linker, which combines the two parts together, and as a spacer, which allows each of the two parts to form its own biological structure and not interfere with the other part. Furthermore, the junction region should create an epitope that will not be recognized by the subject's immune system as foreign, in other words, will not be considered immunogenic. Linker selection may also have an effect on binding activity, and thus the bioactivity, of the fusion protein. (See Huston, et al, 1988, *PNAS*, 85:16:5879-83; Robinson & Bates, 1998, *PNAS* 95 (11):5929-34; and Arai, et al. 2001, *PEDS*, 14 (8):529-32; Chen, X. et al., 2013, *Advanced Drug Delivery Reviews* 65:1357-1369.) In one embodiment, the apelin peptide is connected to the C-terminus or to the N-terminus of the light chain or heavy chain of the antibody or antigen-binding fragment thereof, via one or more peptide linkers.

The antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the disclosure in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al., 1998, *Proc. Natl. Acad. Sci.* (*USA*) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In another aspect, the antibody may be engineered at its Fc domain to activate all, some, or none of the normal Fc effector functions, without affecting the antibody's desired pharmacokinetic properties. Therefore, antibodies with engineered Fc domains that have altered Fc receptor binding may have reduced side effects. Thus, in one embodiment, the protein comprises a chimeric or otherwise modified Fc domain. For an example of a chimeric Fc domain, see International Publication No. WO 2014/121087 A1, published Aug. 7, 2014, which is herein incorporated by reference in its entirety.

The term "$EC_{50}$" or "EC50", as used herein, refers to the half maximal effective concentration, which includes the concentration of a ligand that induces a response, for example a cellular response, halfway between the baseline and maximum after a specified exposure time. The $EC_{50}$ essentially represents the concentration of a ligand where 50% of its maximal effect is observed. Thus, with regard to cellular signaling, increased receptor activity is observed with a decreased $EC_{50}$ value, i.e. half maximal effective concentration value (less ligand needed to produce a greater response).

The term "$IC_{50}$" or "IC50", as used herein, refers to the half maximal inhibitory concentration of a cellular response. In other words, the measure of the effectiveness of a particular moiety (e.g. protein, compound, or molecule) in inhibiting biological or biochemical receptor function, wherein an assay quantitates the amount of such moiety needed to inhibit a given biological process. Thus, with regard to cellular signaling, a greater inhibitory activity is observed with a decreased $IC_{50}$ value.

Methods for Treating or Ameliorating Vascular Eye Diseases or Disorders

The present disclosure includes methods for treating, preventing, or ameliorating at least one symptom or indication of a vascular eye disease or disorder in a subject. The methods according to this aspect of the disclosure comprise administering a therapeutically effective amount of a pharmaceutical composition comprising an APLNR antagonist to the subject in need thereof. In some embodiments, the APLNR antagonist is administered subcutaneously, intravenously or intravitreally. In embodiments, the APLNR antagonist is administered in combination with a VEGF antagonist. In some embodiments, the APLNR antagonist is intravitreally administered in combination with the VEGF antagonist. In some embodiments, the APLNR antagonist is administered as a single combined dosage formulation with the VEGF antagonist. In some embodiments, the APLNR antagonist is administered in combination with the VEGF antagonist, wherein the APLNR antagonist is administered intravenously and the VEGF antagonist is administered intravitreally. The VEGF antagonist may be administered before, after or concurrently with the APLNR antagonist.

The present invention is based, in part, on Applicant's discovery that a combination of antagonism directed against both VEGF and the apelin/APLNR pathways can advantageously impact unwanted pathological vascularization of the eye. In particular, Applicant has discovered that such combinations can be used to treat or prevent conditions such as diabetic retinopathy, including proliferative diabetic retinopathy, retinopathy of prematurity, and age-related macular degeneration. The addition of an antagonist of APLNR can improve the anti-angiogenic effects of VEGF antagonism where antagonism of the VEGF pathway has been saturated.

As used herein, the terms "treat", "treating", or the like, mean to alleviate symptoms, eliminate the causation of symptoms either on a temporary or permanent basis, or to prevent or slow the appearance of symptoms of a neovascular eye disease or disorder. In certain embodiments, the present methods are useful for treating or ameliorating at least one symptom or indication including, but not limited to, retinal angiogenesis, neovascularization, vascular leak, retinal thickening within 500 μm of the center of the fovea, hard, yellow exudates within 500 μm of the center of the fovea with adjacent retinal thickening, and at least 1 disc area of retinal thickening, any part of which is within 1 disc diameter of the center of the fovea, blurry vision, floaters, loss of contrast, double vision, and eventual loss of vision. In the context of methods for treating a vascular eye disease such as AMD or DME, the term means that, from the initiation of treatment, the subject exhibits gain of one or more (e.g., 1, 2, 3, 4, 5, 6, 7, 8, 9, 10 or more) letters on the Early Treatment Diabetic Retinopathy Study (EDTRS) visual acuity chart. In certain embodiments, the term means that, from initiation of treatment, vision loss of greater than or equal to 15 letters is prevented in the subject.

As used herein, the terms "prevent", "preventing", or the like, mean to prevent development of a symptom, indication or a complication of a vascular eye disease. In the context of methods for treating a vascular eye disease such as AMD or DME, the term means, from initiation of treatment, moderate or severe vision loss is prevented in a subject.

As used herein, a "vascular eye disease or disorder" refers to eye disease or disorders that affect blood vessels in the eye. The diseases may be caused due to abnormal angiogenesis (formation of new blood vessels) or occlusion or blockage of blood vessels. The term, as used herein, includes eye diseases or disorders associated with angiogenesis. The term includes, but is not limited to eye disease or disorder selected from the group consisting of diabetic retinopathy (including proliferative diabetic retinopathy), diabetic macular edema, age-related macular degeneration, retinal neovascularization, central retinal vein occlusion, branched retinal vein occlusion, polypoidal choroidal vasculopathy, choroidal neovascularization (CNV), degenerative myopia (myopic CNV), neovascular glaucoma, and retinopathy of prematurity. In certain embodiments, the term "neovascular eye disease or disorder" may be used interchangeably with the term "eye disease or disorder associated with angiogenesis."

In certain embodiments, the present disclosure includes methods for treating, preventing, or ameliorating at least one symptom or indication of an eye disease or disorder associated with angiogenesis in a subject, wherein the disease or disorder is selected from the group consisting of pathological neovascularization, diabetic retinopathy (including proliferative diabetic retinopathy), diabetic macular edema, age-related macular degeneration, retinal neovascularization, polypoidal choroidal vasculopathy, choroidal neovascularization (CNV), degenerative myopia (myopic CNV), neovascular glaucoma, and retinopathy of prematurity. In certain embodiments, administration of an APLNR antagonist also promotes normal revascularization of the retina, for example in oxygen induced retinopathy (O1R).

"Diabetic Macular Edema" (DME), as used herein, refers to a serious eye condition that affects people with diabetes (type 1 or 2). Macular edema occurs when blood vessels in the retina leak into the macula, and fluid and protein deposits collect on or under the macula of the eye (a yellow central area of the retina) which cause it to thicken and swell (edema). The swelling may distort a person's central vision, as the macula is near the center of the retina at the back of the eyeball. The primary symptoms of DME include, but are not limited to, blurry vision, floaters, loss of contrast, double vision, and eventual loss of vision. The pathology of DME is characterized by breakdown of the blood-retinal barrier, normally preventing water movement in the retina, thus allowing fluid to accumulate in the retinal tissue, and presence of retinal thickening. DME is presently diagnosed during an eye examination consisting of a visual acuity test, which determines the smallest letters a person can read on a standardized chart, a dilated eye exam to check for signs of the disease, imaging tests such as optical coherence tomography (OCT) or fluorescein angiography (FA) and tonometry, an instrument that measures pressure inside the eye. The following studies are also performed to determine treatment: optical coherence tomography (OCT), fluorescein angiography, and color stereo fundus photography. DME can be broadly characterized into two main categories— Focal and Diffuse. Focal DME is characterized by specific areas of separate and distinct leakage in the macula with sufficient macular blood flow. Diffuse DME results from leakage of the entire capillary bed surrounding the macula, resulting from a breakdown of the inner blood-retina barrier of the eye. In addition to Focal and Diffuse, DME is also categorized based on clinical exam findings into clinically significant macular edema (CSME), non-CSME and CSME with central involvement (CSME-CI), which involves the fovea. The present disclosure includes methods to treat the above-mentioned categories of DME.

Age-related macular degeneration (AMD), as used herein, refers to a serious eye condition when the small central portion of the retina, known as the macula, deteriorates. The wet form of AMD is characterized by the growth of abnormal blood vessels from the choroid underneath the macula. This is called choroidal neovascularization (CNV). These blood vessels leak blood and fluid into the retina, causing distortion of vision that makes straight lines look wavy, as well as blind spots and loss of central vision. These abnormal blood vessels eventually scar, leading to permanent loss of central vision. The symptoms of AMD include dark, blurry areas in the center of vision; and diminished or changed color perception. AMD can be detected in a routine eye exam. One of the most common early signs of macular degeneration is the presence of drusen—tiny yellow deposits under the retina—or pigment clumping.

"Retinopathy of Prematurity" (ROP), as used herein, also known as retrolental fibroplasia and Terry syndrome, refers to a condition affecting premature infants of low birth weight and young gestational age. Retinopathy of prematurity occurs when the development of normal retinal blood vessels is interrupted by birth prior to full gestational term, resulting in abnormal development of retinal blood vessels. If the condition progresses, the growth of scar tissue can lead to retinal detachment and vision impairment or vision loss. The pathogenesis of ROP involves two discrete phases: a vasoobliterative phase and a vasoproliferative phase. Normal retinal vascular growth is retarded in the first phase as a consequence of exposure to a hyperoxic environment, whereas the second phase includes a rapid increase in neovascularization, followed by retinal detachment. Ablation of the avascular retina by cyrotherapy or laser photocoagulation has been regarded as the primary treatment for ROP, and anti-VEGF therapies (e.g., anti-VEGF antibodies) are being studied. In spite of these treatment options, the condition remains a leading cause of lifelong visual impairment, with an incidence rate that has remained relatively constant for more than twenty years.

Diabetic retinopathy (DR), as used herein, is a chronic progressive disease of the retinal microvasculature associated with prolonged hyperglycemia. DR is the most common microvascular complication of diabetes and is a burgeoning global problem as the prevalence of diabetes mellitus continues to increase worldwide. Proliferative DR (PDR), as used herein, is a sight-threatening complication of DR and is characterized by the development of abnormal new vessels in the retina, optic nerve head or anterior segment of the eye. PDR is the advanced stage of DR, which is driven by hypoxia and expression of proangiogenic growth factors, which stimulate the aberrant formation of new blood vessels in the retina that protrude into the preretinal space. Retinal neovascularization can result in sever vision loss when it leads to vitreous hemorrhage or tractional retinal detachment. Laser photocoagulation has been the standard for treatment of PDR for many years, with more recent therapies including intraocular treatment with anti-VEGF (e.g., anti-VEGF antibodies) and steroid agents, and vitreoretinal surgery. In spite of these therapeutic advances, unmet treatment needs remain, especially noninvasive, nondestructive and longer duration treatment options.

As used herein, the expression "a subject in need thereof" means a human or non-human mammal that exhibits one or more symptoms or indications of, and/or who has been diagnosed with an eye disease or disorder associated with angiogenesis. The term "a subject in need thereof" may also include, e.g., subjects who, prior to treatment, exhibit (or have exhibited) one or more indications of a neovascular eye disease such as, e.g., retinal angiogenesis, neovascularization, vascular leak, retinal thickening within 500 μm of the center of the fovea, hard, yellow exudates within 500 μm of the center of the fovea with adjacent retinal thickening, and at least 1 disc area of retinal thickening, any part of which is within 1 disc diameter of the center of the fovea, blurry vision, floaters, loss of contrast, double vision, and eventual loss of vision.

In the context of the disclosure, a "subject in need thereof" also includes a human or non-human mammal who has a vascular eye disease or disorder selected from the group consisting of diabetic retinopathy (including proliferative diabetic retinopathy), diabetic macular edema, age-related macular degeneration, retinal neovascularization, central retinal vein occlusion, branched retinal vein occlusion, polypoidal choroidal vasculopathy, choroidal neovascularization (CNV), degenerative myopia (myopic CNV), neovascular glaucoma, and retinopathy of prematurity.

In the context of the present disclosure, "a subject in need thereof" may include a subset of population which is more susceptible to DME or AMD or may show an elevated level of a DME-associated or an AMD-associated biomarker, or a biomarker associated with ROP or PDR. For example, "a subject in need thereof" may include a subject suffering from diabetes for more than 10 years, or a subject who has frequent high blood sugar levels or high fasting blood glucose levels. In certain embodiments, the term "a subject in need thereof" includes a subject who, prior to or at the time of administration of the APLNR antagonist and/or VEGF antagonist, has been or is diagnosed with diabetes. In certain embodiments, the term "a subject in need thereof" includes a subject who, prior to or at the time of administration of the APLNR antagonist and/or VEGF antagonist, is more than 50 years old. In some embodiments, the term "a subject in need thereof" includes subjects who are smokers, or subjects with high blood pressure or high cholesterol.

The present disclosure includes methods for treating, preventing or reducing the severity of a vascular eye disease comprising administering a therapeutically effective amount of a pharmaceutical composition comprising an APLNR antagonist in combination with a VEGF antagonist to a subject in need thereof, wherein the pharmaceutical composition is administered to the subject in multiple doses, e.g., as part of a specific therapeutic dosing regimen. For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, the therapeutic dosing regimen may comprise administering multiple doses of the pharmaceutical composition to the subject at a frequency of once a day or 2 times a day or more.

The present disclosure also includes methods for inhibiting or reducing or suppressing vascular leak in a subject. In certain embodiments, the methods according to this aspect of the disclosure comprise administering to the subject one or more doses of a pharmaceutical composition comprising an APLNR antagonist in combination with a VEGF antagonist to reduce or inhibit vascular leak in the eye of a subject. In certain embodiments, the vascular leak is inhibited for more than 3 weeks, more than 4 weeks, more than 8 weeks, or more than 10 weeks compared to a subject who has been administered the VEGF antagonist alone.

The methods of the present disclosure, according to certain embodiments, comprise administering to a subject a therapeutically effective amount of a pharmaceutical composition comprising an APLNR antagonist in combination with a VEGF antagonist. In certain embodiments, the APLNR antagonist may be administered in combination with therapy including laser treatment to stop leakage into the macula. As used herein, the phrase 'in combination with" means that the pharmaceutical composition comprising an APLNR antagonist is administered to the subject at the same time as, just before, or just after administration of a VEGF antagonist. As used herein, the phrase 'in combination with" means that the pharmaceutical composition comprising an APLNR antagonist is administered to the subject at the same time as, just before, or just after administration of the VEGF antagonist. In certain embodiments, the VEGF antagonist is administered as a co-formulation with the APLNR antagonist. In a related embodiment, the present disclosure includes methods comprising administering a therapeutically effective amount of a pharmaceutical composition comprising an APLNR antagonist to a subject to provide a greater therapeutic effect or synergistic effect as compared to administration of the VEGF antagonist alone. The subject may be on a therapeutic regimen of intravitreally administered VEGF antagonist. In some embodiments, the APLNR antagonist is added to this therapeutic regimen, wherein one or more intravitreal injections of the VEGF antagonist may be reduced or the duration between successive intravitreal injections may be increased.

The methods of the present disclosure are useful for treating or preventing vascular eye disorders in subjects that have been diagnosed with or are at risk of being afflicted with a vascular eye disorder. Generally, the methods of the present disclosure demonstrate efficacy within 36 weeks of the initiation of the treatment regimen (with the initial dose administered at "week 0"), e.g., by the end of week 6, by the end of week 12, by the end of week 18, by the end of week 24, etc. In the context of methods for treating angiogenic eye disorders such as AMD, and DME, "efficacy" means that, from the initiation of treatment, the subject exhibits a loss of 10 or fewer letters on the Early Treatment Diabetic Retinopathy Study (ETDRS) visual acuity chart. In certain embodiments, "efficacy" means a gain of one or more (e.g., 1, 2, 3, 4, 5, 6, 7, 8, 9, 10, 11 or more) letters on the ETDRS chart from the time of initiation of treatment.

For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, the therapeutic dosing regimen may comprise administering multiple doses of the pharmaceutical composition to the subject at a frequency of once a day or 2 times a day or more.

APLNR Antagonists

The present disclosure includes methods for treating, preventing, or ameliorating at least one symptom or indication of a vascular eye disease or disorder in a subject comprising administering a therapeutically effective amount of a pharmaceutical composition comprising an APLNR antagonist to the subject in need thereof. The APLNR antagonists include antibodies or antigen-binding fragments thereof, small molecule inhibitors of the apelin receptor signaling pathway, and peptide inhibitors of the apelin receptor signaling pathway. Exemplary small molecule inhibitors or antagonists of APLNR can be found in U.S. Patent Publication Nos. US2014000518 and US20150125459 and International Patent Publication Nos. WO2004081198 and WO2015140296. Exemplary peptide inhibitors or antagonists of APLNR can be found in U.S. Pat. Nos. 9,593,153 and 7,736,646 and International Patent Publication WO2004081198. Other APLNR antagonists include MM54, MM07, N-alpha-acetyl-nona-D-arginine amide acetate (ALX40-4C), ML221, the mutant apelin-13(F13A), 4-oxo-6-((pyrimidin-2-ylthio) methyl)-4H-pyran-3-yl-4-nitrobenzoate (MI221) and E339-3D6.

The APLNR antagonists include antibodies or antigen-binding fragments thereof selected from the group of antibodies disclosed in International Patent Publication No. WO 2015077491, published May 5, 2015, which is specifically incorporated herein in its entirety and U.S. Pat. No. 9,493,554. In some embodiments, the antibodies are H2aM9232N, H4H9232N or H1M9207N. In one embodiment, the anti-APLNR antibody is H4H9232N.

The APLNR antagonists include antibodies, or antigen-binding fragments thereof, selected from the group comprising a heavy chain variable region (HCVR) having an amino acid sequence selected from the group consisting of SEQ ID NO: 2 and 13, or a substantially similar sequence thereof having at least 90%, at least 95%, at least 98% or at least 99% sequence identity.

The APLNR antagonists include antibodies or antigen-binding fragments thereof comprising a light chain variable region (LCVR) having an amino acid sequence selected from the group consisting of SEQ ID NO: 7 and 18, or a substantially similar sequence thereof having at least 90%, at least 95%, at least 98% or at least 99% sequence identity.

According to certain embodiments, the antibody or antigen-binding fragment thereof comprises the heavy and light chain CDR sequences encoded by the nucleic acid sequences of SEQ ID NOs: 1 and 6 (e.g. H1M9207N), and SEQ ID NOs: 12 and 17 (e.g. H2aM9232N or H4H9232N).

Certain non-limiting, exemplary antibodies and antigen-binding fragments of the disclosure comprise HCDR1-HCDR2-HCDR3-LCDR1-LCDR2-LCDR3 domains, respectively, having the amino acid sequences selected from the group consisting of: SEQ ID NOs: 3-4-5-8-9-10 (e.g. H1M9207N), and SEQ ID NOs: 14-15-16-19-20-21 (e.g. H2aM9232N or H4H9232N). The antibodies designated H2aM9232N and H4H9232N share the same human variable regions (HCVR and LCVR). H2aM9232N comprises a murine IgG2a heavy chain constant region, while H4H9232N comprises a human IgG4 heavy chain constant region.

The APLNR antagonists include antibodies or antigen-binding fragments thereof comprising a HCVR and LCVR (HCVR/LCVR) sequence pair selected from the group consisting of SEQ ID NO: 2/7, and 13/18.

The APLNR antagonists include antibodies or antigen-binding fragments thereof comprising a heavy chain CDR3 (HCDR3) domain having an amino acid sequence selected from the group consisting of SEQ ID NO: 5 and 16, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 10 and 21, or a substantially similar sequence thereof having at least 90%, at least 95%, at least 98% or at least 99% sequence identity.

In certain embodiments, The APLNR antagonists include antibodies or antigen-binding fragments thereof comprises a HCDR3/LCDR3 amino acid sequence pair selected from the group consisting of SEQ ID NO: 5/10 and 16/21.

The APLNR antagonists include antibodies or antigen-binding fragments thereof comprising a heavy chain CDR1 (HCDR1) domain having an amino acid sequence selected from the group consisting of SEQ ID NO: 3 and 14, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 4 and 15, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 8 and 19, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 9 and 20, or a substantially similar sequence thereof having at least 90%, at least 95%, at least 98% or at least 99% sequence identity.

Certain non-limiting, exemplary anti-APLNR antibodies include an antibody or antigen-binding fragment of an antibody that specifically binds APLNR, wherein the antibody or antigen-binding fragment comprises the heavy and light chain CDR domains contained within heavy and light chain variable region (HCVR/LCVR) sequences selected from the group consisting of SEQ ID NO: 2/7 and 13/18.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., 1997, *J. Mol. Biol.* 273:927-948; and Martin et al., 1989, *Proc. Natl. Acad. Sci. USA* 86:9268-9272. Public databases are also available for identifying CDR sequences within an antibody.

The present disclosure provides antibodies or antigen-binding fragments thereof comprising a heavy chain (HCVR) having an amino acid sequence selected from the group consisting of SEQ ID NO: 2 and 13, or a substantially similar sequence thereof having at least 90%, at least 95%, at least 98% or at least 99% sequence identity.

The present disclosure also provides an antibody or antigen-binding fragment of an antibody comprising a light chain (LCVR) having an amino acid sequence selected from the group consisting of SEQ ID NO: 7 and 18, or a substantially similar sequence thereof having at least 90%, at least 95%, at least 98% or at least 99% sequence identity.

The present disclosure also provides an antibody or antigen-binding fragment thereof comprising a HC and LC (HC/LC) amino acid sequence pair.

According to certain embodiments, the antibody or antigen-binding fragment thereof comprises the heavy and light chain CDR sequences encoded by the nucleic acid sequences of antibodies H1M9207N, or H2aM9232N (or H4H9232N).

The present disclosure includes anti-APLNR antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al., 2002, *JBC* 277:26733). In other applications, modification of galactosylation can be made in order to modify complement dependent cytotoxicity (CDC).

For example, the present disclosure includes APLNR antagonists thereof that block or inhibit apelin-mediated signaling in cells expressing human APLNR, with an $IC_{50}$ of less than about 20 nM, less than about 10 nM, less than about 2 nM, less than about 1 nM, less than about 900 pM, less than about 800 pM, less than about 700 pM, less than about 600 pM, less than about 500 pM, less than about 400 pM, less than about 350 pM, less than about 300 pM, less than about 250 pM, less than about 200 pM, less than about 150 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured in a cell-based blocking or inhibition bioassay, e.g., using the assay format as defined in Examples 5, 8, 9 or 11 of WO2015/077491, or a substantially similar assay.

The present disclosure includes APLNR antagonists that inhibit APLNR-mediated ratio of pERK, in the presence of apelin, with an $IC_{50}$ of less than about 50 nM, less than about 25 nM, less than about 20 nM, less than about 15 nM, less than about 10 nM, less than about 5 nM, less than about 1 nM, less than about 900 pM, less than about 800 pM, less than about 700 pM, less than about 600 pM, less than about 500 pM, less than about 400 pM or less than about 300 pM, as measured in an APLNR-induced pERK assay.

In other embodiments, however, certain APLNR antagonists of the present disclosure, despite having the ability to inhibit or attenuate APLNR-mediated signaling, do not block or only partially block the interaction of APLNR and apelin. Such antibodies and antigen-binding fragments thereof, may be referred to herein as "indirect blockers." Without being bound by theory, it is believed that the indirect blockers of the disclosure function by binding to APLNR at an epitope that does not overlap, or overlaps only partially, with the N-terminal ligand binding domain of APLNR, but nonetheless interferes with APLNR-mediated signaling without blocking the APLNR/apelin interaction directly.

The present disclosure includes APLNR antagonists that bind soluble APLNR molecules with high affinity and/or specificity. For example, the present disclosure includes antibodies and antigen-binding fragments of antibodies that bind APLNR with a binding ratio of greater than about 20 as measured by a fluorescent activated cell sorting (FACS) assay, e.g., using the assay format as defined in Example 4 of WO2015/077491. In certain embodiments, the antibodies or antigen-binding fragments of the present disclosure bind APLNR with a binding ratio of greater than about 15, greater than about 20, greater than about 100, greater than about 200, greater than about 300, greater than about 400, greater than about 500, greater than about 1000, greater than about 1500, or greater than about 2000, as measured by e.g., FACS, or a substantially similar assay.

The present disclosure also includes anti-APLNR antibodies and antigen-binding fragments thereof that specifically bind to APLNR with a dissociative half-life (t½) of greater than about 10 minutes as measured by surface plasmon resonance at 25° C. or 37° C., e.g., using the well-known BIAcore™ assay format, or a substantially similar assay.

The antibodies of the present disclosure may possess one or more of the aforementioned biological characteristics, or any combinations thereof. Other biological characteristics of the antibodies of the present disclosure will be evident to a person of ordinary skill in the art from a review of the present disclosure including the working Examples herein.

The anti-APLNR antibodies may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antibodies and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies, and antigen-binding fragments obtained in this general manner are encompassed within the present disclosure.

The present disclosure also includes anti-APLNR antibodies comprising variants of any of the HCVR, LCVR, and/or CDR amino acid sequences disclosed herein having one or more conservative substitutions. For example, the present disclosure includes anti-APLNR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, 1994, *Methods Mol. Biol.* 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., 1992, *Science* 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, 1994, supra). Another preferred algorithm when comparing a sequence of the disclosure to a database containing a large number of sequences from different organisms is the computer program BLAST, especially BLASTP or TBLASTN, using default parameters. See, e.g., Altschul et al., 1990, *J. Mol. Biol.* 215:403-410 and Altschul et al., 1997, *Nucleic Acids Res.* 25:3389-402, each herein incorporated by reference.

The present disclosure further includes anti-APLNR antibodies that bind to the same epitope as any of the specific exemplary antibodies described herein (e.g. H1M9207N and H2aM9232N and H4H9232N). Likewise, the present disclosure also includes anti-APLNR antibodies that compete for binding to APLNR with any of the specific exemplary antibodies described herein (e.g. H1M9207N and H2aM9232N and H4H9232N).

One can easily determine whether an antibody binds to the same epitope as, or competes for binding with, a reference anti-APLNR antibody by using routine methods known in the art and exemplified herein. For example, to determine if a test antibody binds to the same epitope as a reference anti-APLNR antibody of the disclosure, the reference antibody is allowed to bind to an APLNR protein. Next, the ability of a test antibody to bind to the APLNR molecule is assessed. If the test antibody is able to bind to APLNR following saturation binding with the reference anti-APLNR antibody, it can be concluded that the test antibody binds to a different epitope than the reference anti-APLNR antibody. On the other hand, if the test antibody is not able to bind to the APLNR molecule following saturation binding with the reference anti-APLNR antibody, then the test antibody may bind to the same epitope as the epitope bound by the reference anti-APLNR antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, BIAcore™, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., 1990, *Cancer Res.* 50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-APLNR antibody, the above-described binding methodology is performed in two orientations: In a first orientation, the reference antibody is allowed to bind to an APLNR protein under saturating conditions followed by assessment of binding of the test antibody to the APLNR molecule. In a second orientation, the test antibody is allowed to bind to an APLNR molecule under saturating conditions followed by assessment of binding of the reference antibody to the APLNR molecule. If, in both orientations, only the first (saturating) antibody is capable of binding to the APLNR molecule, then it is concluded that the test antibody and the reference antibody compete for binding to APLNR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

In certain embodiments of the disclosure, the anti-APLNR antibodies of the disclosure are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. In various embodiments, the antibodies discussed herein are human antibodies with an IgG heavy chain constant region. In some cases, the antibodies have a heavy chain constant region of human IgG1 or IgG4 isotype.

The antibodies of the disclosure may, in some embodiments, be recombinant human antibodies. The term "recombinant human antibody", as used herein, is intended to include all human antibodies thereof that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., 1992, *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al., 1993, *Molecular Immunology* 30:105) to levels typically observed using a human IgG1 hinge. The instant disclosure encompasses antibodies having one or more mutations in the hinge, $C_H2$ or $C_H3$ region which may be desirable, for example, in production, to improve the yield of the desired antibody form.

The antibodies of the disclosure may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present disclosure includes neutralizing and/or blocking anti-APLNR antibodies. A "neutralizing" or "blocking" antibody, as used herein, is intended to refer to an antibody whose binding to APLNR: (i) interferes with the interaction between APLNR or an APLNR fragment and an APLNR receptor component (e.g., apelin peptide, etc.); and/or (ii) results in inhibition of at least one biological function of APLNR. The inhibition caused by an APLNR neutralizing or blocking antibody need not be complete so long as it is detectable using an appropriate assay.

VEGF Antagonists

As used herein, a "VEGF antagonist" is any agent that binds to or interacts with VEGF, inhibits the binding of VEGF to its receptors (VEGFR1 and VEGFR2), and/or inhibits the biological signaling and activity of VEGF. VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies (e.g., ranibizumab [LUCENTIS®]), anti-VEGF receptor antibodies (e.g., anti-VEGFR1 antibodies, anti-VEGFR2 antibodies, etc.), small molecule inhibitors of VEGF (e.g., sunitinib), and VEGF receptor-based chimeric molecules or VEGF-inhibiting fusion proteins (also referred to herein as "VEGF-Traps"), such as aflibercept and ziv-aflibercept. Other examples of VEGF-Traps are ALT-L9, M710, FYB203 and CHS-2020. Additional examples of VEGF-Traps can be found in U.S. Pat. Nos. 7,070,959, 7,306,799, 7,374,757, 7,374,758, 7,531,173, 7,608,261, 5,952,199, 6,100,071, 6,383,486, 6,897,294 and 7,771,721, which are specifically incorporated herein by reference. Additional VEGF inhibitors and/or antagonist include the small molecules inhibitors: pazopanib, sorafenib, axitinib, ponatinib, regorafenib, cabozantinib, vandetanib, cabozantinib, and lenvatinib; and VEGF inhibitory antibodies: bevacizumab and ramucirumab, or biosimilar molecules thereof.

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) (also known as aflibercept; marketed under the product name EYLEA®). In certain embodiments, aflibercept comprises the amino acid sequence set forth as

```
                                        (SEQ ID NO: 23)
MVSYWDTGVLLCALLSCLLLTGSSSGSDTGRPFVEMYSEIPEIIHMTEGR

ELVIPCRVTSPNITVTLKKFPLDTLIPDGKRIIWDSRKGFIISNATYKEI

GLLTCEATVNGHLYKTNYLTHRQTNTIIDVVLSPSHGIELSVGEKLVLNC

TARTELNVGIDFNWEYPSSKHQHKKLVNRDLKTQSGSEMKKFLSTLTIDG

VTRSDQGLYTCAASSGLMTKKNSTFVRVHEKDKTHTCPPCPAPELLGGPS

VFLFPPKPKDTLMISRTPEVTCVVVDVSHEDPEVKFMWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPGK.
```

The amount of the VEGF antagonist contained within the pharmaceutical formulations of the present disclosure may vary depending on the specific properties desired of the formulations, as well as the particular circumstances and purposes for which the formulations are intended to be used. In certain embodiments, the pharmaceutical formulations are liquid formulations that may contain 5±0.75 mg/mL to 150±22.5 mg/mL of VEGF antagonist; 10±1.5 mg/mL to 100±15.0 mg/mL of VEGF antagonist; 20±3 mg/mL to 80±12 mg/mL of VEGF antagonist; 30±4.5 mg/mL to 70±10.5 mg/mL of VEGF antagonist or 40±6.0 mg/mL of the VEGF antagonist. For example, the formulations of the present disclosure may comprise about 20 mg/mL; about 30 mg/mL; about 40 mg/mL; about 50 mg/mL; or about 60 mg/mL of a VEGF antagonist.

The methods of the present disclosure comprise administering to a subject in need thereof a therapeutic composition comprising an VEGF antagonist.

Therapeutic Formulation and Administration

The present disclosure provides pharmaceutical formulations comprising at least one APLNR antagonist, such as an anti-APLNR antibody, or an antigen-binding fragment thereof, which binds specifically to human APLNR. According to certain other embodiments, the present disclosure provides pharmaceutical formulations comprising additional therapeutic agents. The present disclosure further provides pharmaceutical formulations comprising at least one VEGF antagonist, for example, for use in conjunction with a pharmaceutical formulation comprising at least one APLNR antagonist.

The pharmaceutical compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, 1998, *J Pharm Sci Technol* 52:238-311.

The dose of APLNR antagonist, such as an anti-APLNR antibody, or an antigen-binding fragment thereof, which binds specifically to human APLNR, administered to a subject may vary depending upon the age and the size of the subject, target disease, conditions, route of administration, and the like. The preferred dose is typically calculated according to body weight or body surface area. When an APLNR antagonist is used for treating a condition or disease, it may be advantageous to intravenously administer the antibody of the present disclosure normally at a single dose of about 0.01 to about 50 mg/kg body weight. In other instances it may be advantageous to administer an APLNR antagonist intravitreally, for example at a concentration of about 0.01 to about 50 mg/kg body weight. Depending on the severity of the condition, the frequency and the duration of the treatment can be adjusted. Effective dosages and schedules for administering APLNR antagonist, such as anti-APLNR antibodies, may be determined empirically; for example, subject progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

The dose of VEGF antagonist may vary depending upon the age and the size of the subject, target disease, conditions, route of administration, and the like. The preferred dose is typically calculated according to body weight or body surface area. When a VEGF antagonist is used for treating a condition or disease, it may be advantageous to intravenously administer the antibody of the present disclosure normally at a single dose of about 0.01 to about 50 mg/kg body weight. In other instances it may be advantageous to administer a VEGF antagonist intravitreally, for example at a concentration of about 0.01 to about 50 mg/kg body weight. Depending on the severity of the condition, the frequency and the duration of the treatment can be adjusted. Effective dosages and schedules for administering VEGF antagonist may be determined empirically; for example, subject progress can be monitored by periodic assessment, and the dose adjusted accordingly. Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, intravitreal, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The present disclosure includes methods which comprise administering an APLNR antagonist to a subject wherein the APLNR antagonist is contained within a pharmaceutical composition. In certain embodiments, the pharmaceutical composition further comprises a VEGF antagonist. In alternate embodiments, the APLNR antagonist and the VEGF antagonist may each be in its own separate pharmaceutical dosage formulation. The pharmaceutical compositions of the disclosure may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient or one or more additional inactive ingredients, is suitable for therapeutic administration to a human or non-human animal. The term "formulation", as used herein, means "pharmaceutical formulation" unless specifically indicated otherwise.

The amount of APLNR antagonist, such as anti-APLNR antibody, or antigen-binding fragment thereof, contained within the pharmaceutical formulations of the present disclosure may vary depending on the specific properties desired of the formulations, as well as the particular circumstances and purposes for which the formulations are intended to be used. In certain embodiments, the pharmaceutical formulations are liquid formulations that may contain 5±0.75 mg/mL to 150±22.5 mg/mL of antibody; 7.5±1.125 mg/mL to 140±21 mg/mL of antibody; 10±1.5 mg/mL to 130±19.5 mg/mL of antibody; 10±1.5 mg/mL of antibody; 20±3 mg/mL of antibody; 60±9 mg/mL of antibody; or 120±18 mg/mL of antibody. For example, the formulations of the present disclosure may comprise about 10 mg/mL; about 20 mg/mL; about 40 mg/mL; about 60 mg/mL; about 80 mg/mL; about 100 mg/mL; about 120 mg/mL; or about 140 mg/mL of an antibody or an antigen-binding fragment thereof that binds specifically to human APLNR.

In certain embodiments, the pharmaceutical formulations are liquid formulations that may contain 5±0.75 mg/mL to 100±15 mg/mL of a VEGF antagonist. For example, the formulations of the present disclosure may comprise about 5 mg/mL; about 10 mg/mL; about 15 mg/mL; about 20 mg/mL; about 25 mg/mL; about 30 mg/mL; about 35 mg/mL; about 40 mg/mL; about 50 mg/mL; about 60 mg/mL; about 70 mg/mL; about 80 mg/mL; about 90 mg/mL; or about 100 mg/mL of a VEGF antagonist such as aflibercept.

In certain embodiments, the pharmaceutical formulations are stable liquid co-formulations comprising about 5 mg/mL to about 150 mg/mL of the APLNR antagonist and about 5 to 100 mg/mL of the VEGF antagonist.

The pharmaceutical formulations of the present disclosure comprise one or more excipients. The term "excipient", as used herein, means any non-therapeutic agent added to the formulation to provide a desired consistency, viscosity or stabilizing effect.

Exemplary formulations comprising a VEGF antagonist that can be used in the context of the present disclosure are disclosed, e.g., in U.S. Pat. Nos. 7,531,173 and 7,608,261. Exemplary pharmaceutical compositions comprising an APLNR antagonist that can be used in the context of the present disclosure are disclosed, e.g., in U.S. Patent Application Publication No. 20130186797. Exemplary pharmaceutical compositions comprising an APLNR antagonist that can be used in the context of the present disclosure are disclosed, e.g., in International Patent Publication No. WO2016085750 and US Patent Application Publication No. US20110027286.

Combination Therapies

The methods of the present disclosure, according to certain embodiments, comprise administering to the subject an APLNR antagonist in combination with a VEGF antagonist. As used herein, the expression "in combination with" means that the VEGF antagonist is administered before, after, or concurrent with the pharmaceutical composition comprising the APLNR antagonist. The term "in combination with" also includes sequential or concomitant administration of an APLNR antagonist and a VEGF antagonist. For example, when administered "before," the pharmaceutical composition comprising the APLNR antagonist may be administered more than 72 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the VEGF antagonist. When administered "after," the pharmaceutical composition comprising the APLNR antagonist may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the pharmaceutical composition comprising the VEGF antagonist. Administration "concurrent" with the pharmaceutical composition comprising the APLNR antagonist means that the VEGF antagonist is administered to the subject in a separate dosage form within less than 5 minutes (before, after, or at the same time) of administration of the pharmaceutical composition comprising the APLNR antagonist, or administered to the subject as a single combined dosage formulation comprising the APLNR antagonist and the VEGF antagonist.

Combination therapies may include an APLNR antagonist and a VEGF antagonist (e.g., aflibercept, a VEGF-Trap, see, e.g., U.S. Pat. No. 7,087,411 (also referred to herein as a "VEGF-inhibiting fusion protein"), anti-VEGF antibody (e.g., ranibizumab, etc.), a small molecule kinase inhibitor of VEGF receptor (e.g., sunitinib, sorafenib or pazopanib), etc.

The methods of the disclosure comprise administering an APLNR antagonist in combination with a VEGF antagonist for additive or synergistic activity to treat or ameliorate at least one symptom or indication of an eye disease or disorder selected from the group consisting of diabetic retinopathy (including proliferative diabetic retinopathy), diabetic macular edema, age-related macular degeneration, retinal neovascularization, central retinal vein occlusion, branched retinal vein occlusion, polypoidal choroidal vasculopathy, choroidal neovascularization (CNV), degenerative myopia (myopic CNV), neovascular glaucoma, and retinopathy of prematurity.

Containers and Methods of Administration

Various delivery systems are known and can be used to administer the pharmaceutical composition of the disclosure, e.g., encapsulation in liposomes, micro-particles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, intravitreal, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

For the treatment of eye disorders, the pharmaceutical formulations of the disclosure may be administered, e.g., by eye drops, subconjunctival injection, subconjunctival implant, intravitreal injection, intravitreal implant, sub-Tenon's injection or sub-Tenon's implant.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The pharmaceutical formulations of the present disclosure may be contained within any container suitable for storage or administration of medicines and other therapeutic compositions. For example, the pharmaceutical formulations may be contained within a sealed and sterilized plastic or glass container having a defined volume such as a vial, ampule, syringe, cartridge, bottle, or IV bag. Different types of vials can be used to contain the formulations of the present disclosure including, e.g., clear and opaque (e.g., amber) glass or plastic vials. Likewise, any type of syringe can be used to contain or administer the pharmaceutical formulations of the present disclosure.

The pharmaceutical formulations of the present disclosure may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present disclosure, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present disclosure, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present disclosure are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present disclosure are commercially available under the tradename "FluroTec®", available from West Pharmaceutical Services, Inc. (Lionville, Pa.). FluroTec® is an example of a fluorocarbon coating used to minimize or prevent drug product from adhering to the rubber surfaces.

According to certain embodiments of the present disclosure, the pharmaceutical formulations may be contained within a low tungsten syringe that comprises a fluorocarbon-coated plunger.

The pharmaceutical formulations can be administered to a subject by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany). Examples of disposable pen or autoinjector delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park, Ill.).

The use of a microinfusor to deliver the pharmaceutical formulations of the present disclosure is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., J. Controlled Release 46:107-116 (1996). Microinfusors are particularly useful for the delivery of large doses of therapeutic proteins contained within high concentration (e.g., about 100, 125, 150, 175, 200 or more mg/mL) or viscous solutions.

In one embodiment, the pharmaceutical formulation is administered via an IV drip, such that the formulation is diluted in an IV bag containing a physiologically acceptable solution. In one embodiment, pharmaceutical composition is a compounded sterile preparation in an intravenous infusion bag, such that a single dose of drug product is diluted into 100 mL, 250 mL (or other like amount suitable for intravenous drip delivery) of a physiological buffer (e.g., 0.9% saline). In some embodiments, the infusion bag is made of a polyvinyl chloride (e.g., VIAFLEX, Baxter, Deerfield, Ill.). In some embodiments, the infusion bag is made of a polyolefin (EXCEL IV Bags, Braun Medical Inc., Bethlehem, Pa.).

Administration Regimens

The present disclosure includes methods comprising administering to a subject a pharmaceutical composition comprising an APLNR antagonist, such as an anti-APLNR antibody, or antigen-binding fragment thereof, at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the methods involve the administration of a pharmaceutical composition comprising an APLNR antagonist, such as an anti-APLNR antibody, or antigen-binding fragment thereof, and a VEGF antagonist, at a dosing frequency of about four times a week, twice a week, once a week, once every two weeks, once every three weeks, once every four weeks, once every five weeks, once every six weeks, once every eight weeks, once every nine weeks, once every twelve weeks, or less frequently so long as a therapeutic response is achieved.

According to certain embodiments of the present disclosure, multiple doses of an APLNR antagonist, such as an anti-APLNR antibody, or antigen-binding fragment thereof, and a VEGF antagonist, may be administered to a subject over a defined time course. The methods according to this aspect of the disclosure comprise sequentially administering to a subject multiple doses of an APLNR antagonist, such as an anti-APLNR antibody, or antigen-binding fragment thereof, and a VEGF antagonist. As used herein, "sequentially administering" means that each dose of an APLNR antagonist, such as an anti-APLNR antibody, or antigen-binding fragment thereof, and a VEGF antagonist, is administered to the subject at a different point in time, e.g., on different days separated by a predetermined interval (e.g., hours, days, weeks or months). The present disclosure includes methods which comprise sequentially administering to the subject a single initial dose of an APLNR antagonist, such as an anti-APLNR antibody, or antigen-binding fragment thereof, and a VEGF antagonist, followed by one or more secondary doses of the APLNR antagonist, such as an anti-APLNR antibody, or antigen-binding fragment thereof, and the VEGF antagonist, and optionally followed by one or more tertiary doses of the APLNR antagonist, such as an anti-APLNR antibody, or antigen-binding fragment thereof, and the VEGF antagonist.

According to certain embodiments of the present disclosure, multiple doses of a co-formulation comprising an APLNR antagonist, such as an anti-APLNR antibody, or antigen-binding fragment thereof, and a VEGF antagonist, may be administered to a subject over a defined time course. The methods according to this aspect of the disclosure comprise sequentially administering to a subject multiple doses of a co-formulation comprising an APLNR antagonist, such as an anti-APLNR antibody, or antigen-binding fragment thereof, and a VEGF antagonist. As used herein, "sequentially administering" means that each dose of the APLNR antagonist in combination with the VEGF antagonist is administered to the subject at a different point in time, e.g., on different days separated by a predetermined interval (e.g., hours, days, weeks or months). The present disclosure includes methods which comprise sequentially administering to the subject a single initial dose of a co-formulation comprising an APLNR antagonist and a VEGF antagonist, followed by one or more secondary doses of the co-formulated APLNR antagonist and a VEGF antagonist, and optionally followed by one or more tertiary doses of the co-formulated APLNR antagonist and a VEGF antagonist.

The terms "initial dose," "secondary doses," and "tertiary doses," refer to the temporal sequence of administration. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of APLNR antagonist (or a co-formulation comprising APLNR antagonist and VEGF antagonist), but generally may differ from one another in terms of frequency of administration. In certain embodiments, however, the amount contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an APLNR antagonist (or a co-formulation comprising APLNR antagonist and VEGF antagonist) may be administered to a subject with an eye disease or disorder at a loading dose of about 6 mg followed by one or more maintenance doses.

In one exemplary embodiment of the present disclosure, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of APLNR antagonist (or a co-formulation comprising APLNR antagonist and VEGF antagonist) which is administered to a subject prior to the administration of the very next dose in the sequence with no intervening doses.

The methods according to this aspect of the disclosure may comprise administering to a subject any number of secondary and/or tertiary doses of an anti-APLNR antagonist (or a co-formulation comprising APLNR antagonist and VEGF antagonist). For example, in certain embodiments, only a single secondary dose is administered to the subject. In other embodiments, two or more (e.g., 2, 3, 4, 5, 6, 7, 8, or more) secondary doses are administered to the subject. Likewise, in certain embodiments, only a single tertiary dose is administered to the subject. In other embodiments, two or more (e.g., 2, 3, 4, 5, 6, 7, 8, or more) tertiary doses are administered to the subject.

In embodiments involving multiple secondary doses, each secondary dose may be administered at the same frequency as the other secondary doses. For example, each secondary dose may be administered to the subject 1 to 2 weeks after the immediately preceding dose. Similarly, in embodiments involving multiple tertiary doses, each tertiary dose may be administered at the same frequency as the other tertiary doses. For example, each tertiary dose may be administered to the subject 2 to 4 weeks after the immediately preceding dose. Alternatively, the frequency at which the secondary and/or tertiary doses are administered to a subject can vary over the course of the treatment regimen. The frequency of administration may also be adjusted during the course of treatment by a physician depending on the needs of the individual subject following clinical examination.

The present disclosure includes methods comprising sequential administration of an APLNR antagonist and a VEGF antagonist, to a subject to treat DME, AMD, ROP or PDR. In some embodiments, the present methods comprise administering one or more doses of an APLNR antagonist followed by one or more doses of a VEGF antagonist. In certain embodiments, the present methods comprise administering a single dose of a VEGF antagonist followed by one or more doses of an APLNR antagonist.

EXAMPLES

The following examples are put forth so as to provide those of ordinary skill in the art with a complete disclosure and description of how to make and use the methods and compositions of the disclosure, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

To assess the in vivo characteristics of select anti-APLNR antibodies of the disclosure, their ability to block APLNR-mediated angiogenesis in the eye vasculature was measured.

A retinal vascular development (RVD) model was used to evaluate the effects of an antagonistic anti-APLNR antibody on blood vessel outgrowth in the normal developing retina of mouse pups that were of a mixed background strain (75% C57BL6 and 25% Sv129) and homozygous for expression of human APLNR in place of mouse APLNR (humanized APLNR mice).

Humanized (Hu) ApelinR mice were systemically (IP) injected with 25 mg/kg and 50 mg/kg anti-Apelin Receptor antibody ($\alpha$AR; H2aM9232N) at postnatal day (P)2. Reagents were masked and labeled as Solution A and Solution B to prevent experimenter bias. At postnatal day 5, tissue samples were collected and then fixed in PBS containing 4% paraformaldehyde. Fixed tissue samples (retinal endothelial cells) were washed with PBS, and subsequently stained with GS Lectin I (Vector Laboratories, #FL-1101) diluted 1:200 in 1× PBS containing 1% BSA in 0.25% Triton-X 100 overnight at 25° C. to visualize retinal vasculature. The following day, stained samples were rinsed with PBS several times, flat-mounted onto slides, and coverslips were subsequently mounted using Prolong Gold (Invitrogen, #P36930). Images were taken at 20 times magnification using an epi-fluorescent microscope (Nikon Eclipse 80). The vascularized areas in the retina were measured from acquired images from this assay using Adobe Photoshop CS6 extended. Only after retinal vasculature area measurements and statistical analysis were completed, the sample identities were unmasked.

Figure 1B:
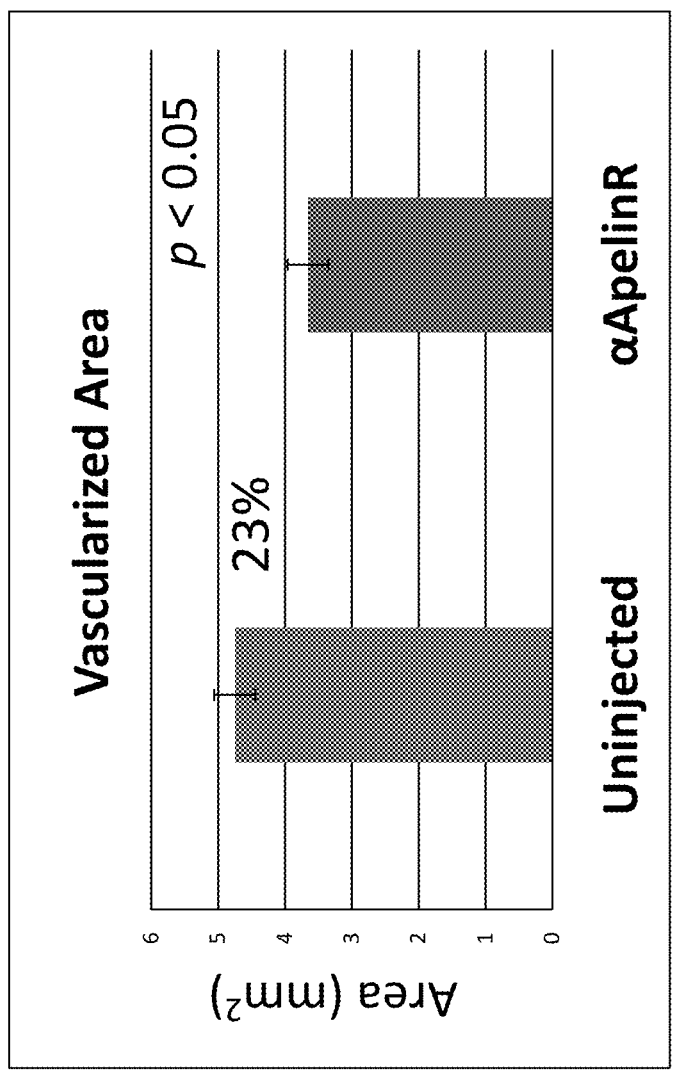

FIGS. 1A and 1B are representative photomicrographs of mouse retinas treated systemically at P2 to P5 and a graph of the calculated vascular area (images at 20×, for quantification, and 40×; statistical analysis was done with Student T-test).

Residual vascular area was significantly smaller in $\alpha$ApelinR (23% at 25 mg/kg, $p<0.05$) retinas compared to untreated retinas. Selective inhibition of ApelinR via systemic injection delayed normal vascular outgrowth in the developing retina in P5 pups. At 25 mg/kg Dose, blocking ApelinR slightly inhibits vascular outgrowth.

Example 2

Figure 2A:
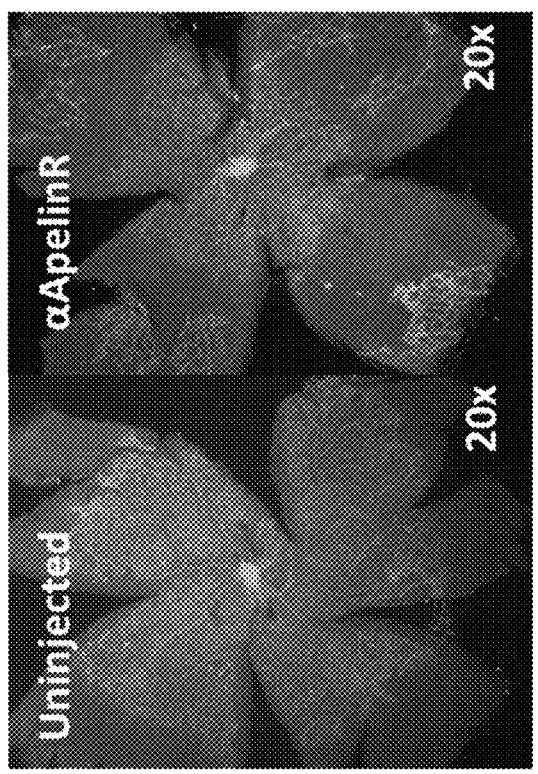
FIGS. 2A and 2B are representative photomicrographs of mouse retinas treated systemically (IP) at P2 to P5 and a graph of the calculated vascular area. Residual vascular area was significantly smaller in αApelinR treated (35% at 50 mg/kg, $p<0.005$) retinas compared to untreated retinas. Retinal endothelial cells were stained with GS Lectin I. Images were taken at 20× (for quantification) and 40×. Statistical analysis was done with Student T-test. Selective inhibition of ApelinR via systemic injection delayed normal vascular outgrowth in the developing retina in P5 pups. By increasing the dose to 50 mg/kg Dose, targeting ApelinR further delays retinal vascular outgrowth.
Figure 2A:
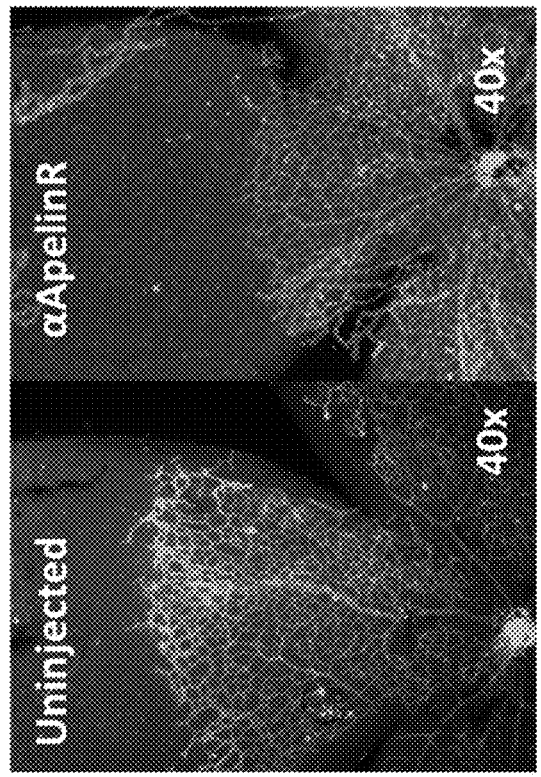
Figure 2B:
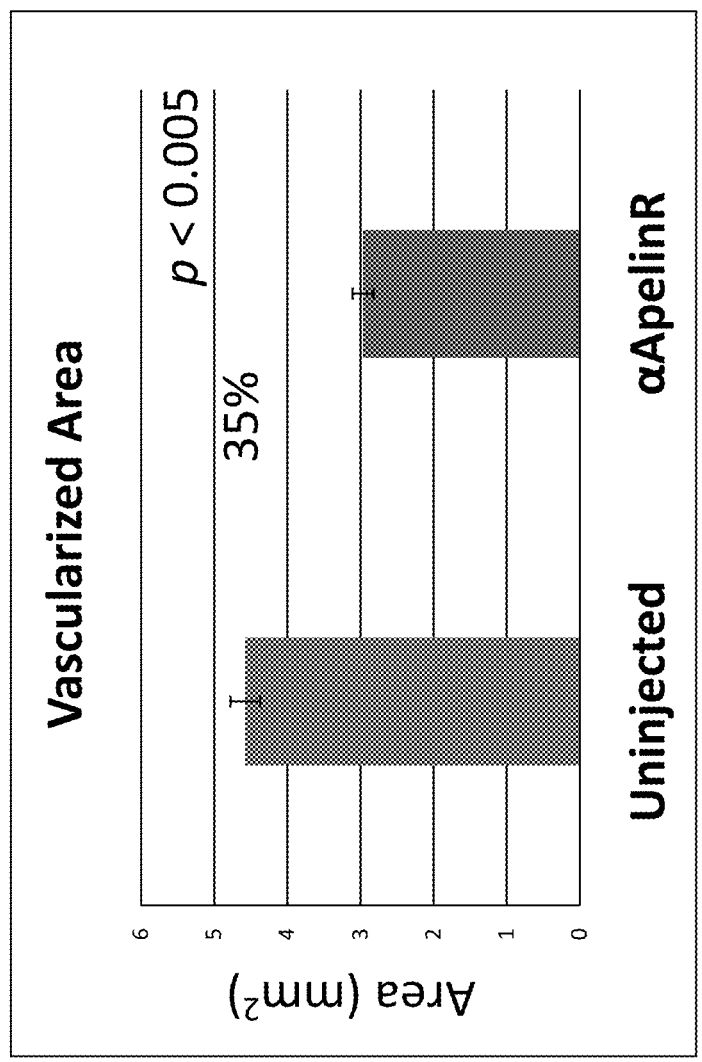

A subsequent experiment in the RVD model was done analogously to Example 1 at the highest dose, and analyzed by masked graders. Briefly, pups were IP injected with 50 mg/kg Fc (control) or $\alpha$AR. FIGS. 2A and 2B are representative photomicrographs of mouse retinas treated systemically at P2 to P5 and a graph of the calculated vascular area. Residual vascular area was significantly smaller in $\alpha$ApelinR (35% at 50 mg/kg, $p<0.005$) retinas compared to untreated retinas. Retinal endothelial cells were stained with GS Lectin I. Images were taken at 20× (for quantification) and 40×. Statistical analysis was done with Student T-test.

Selective inhibition of ApelinR via systemic injection delayed normal vascular outgrowth in the developing retina in P5 pups. By increasing the dose to 50 mg/kg Dose, targeting ApelinR further delays retinal vascular outgrowth.

Example 3

Figure 3A:
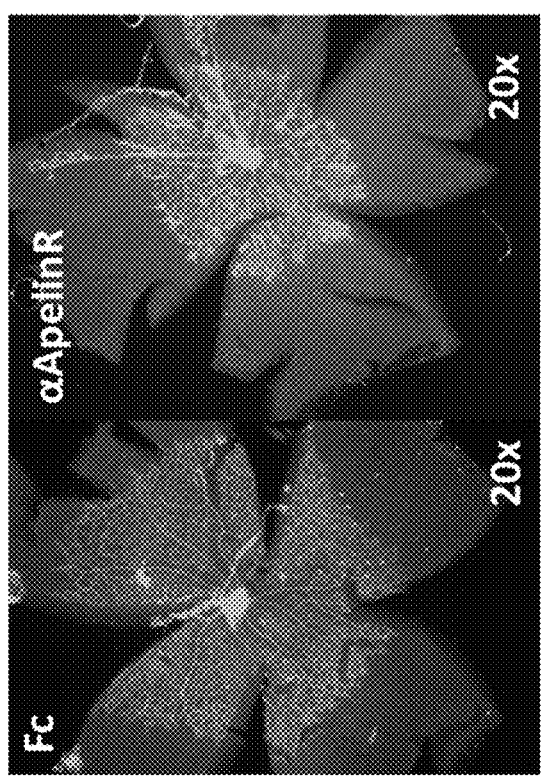
FIGS. 3A and 3B are representative photomicrographs of mouse retinas treated systemically (IP) at P2 to P5 and a graph of the calculated vascular area. In this masked study, 50 mg/kg αApelinR decreased vascular growth by 29.8% ($p<0.0001$) compared to Fc treated controls. Retinal endothelial cells were stained with GS Lectin I. Images were taken at 20× (for quantification) and 40×. Statistical analysis was done with Student T-test. Selective inhibition of ApelinR via systemic injection delays normal vascular outgrowth in the developing retina in P5 pups.
Figure 3A:
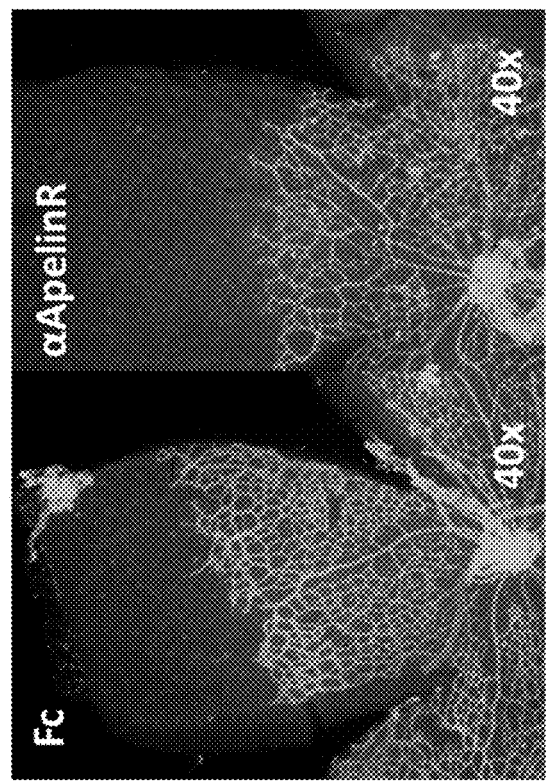
Figure 3B:
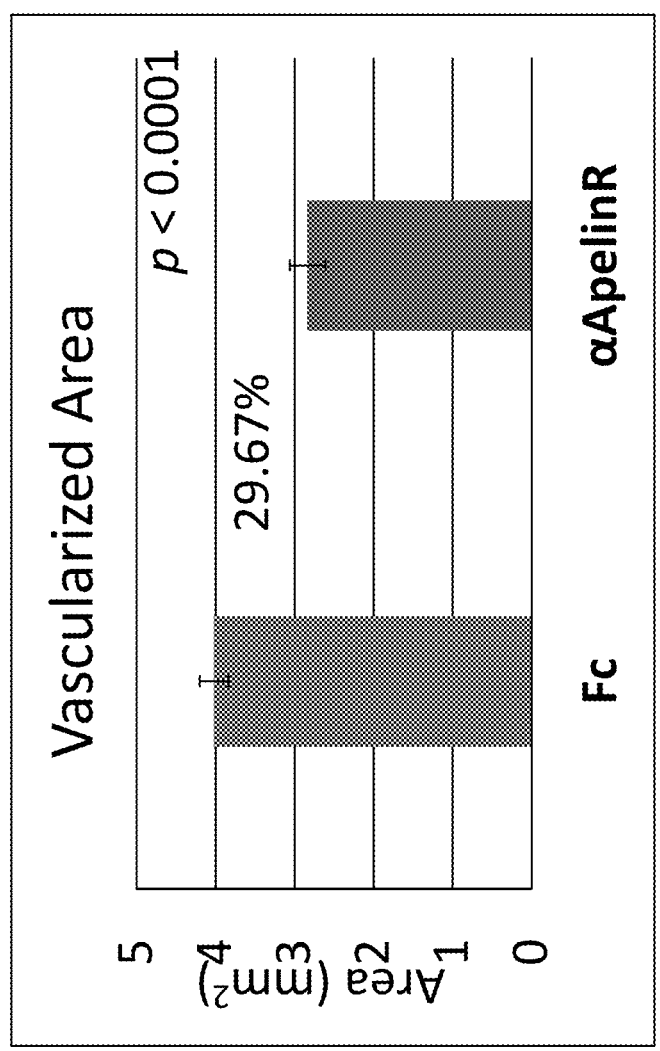

In a subsequent experiment in the RVD model (performed analogously to Example 1), P2 Hu pups were IP injected with 50 mg/kg Fc, αAR or aflibercept or combination (αAR and aflibercept) and collected at P5. FIGS. 3A and 3B are representative photomicrographs of mouse retinas treated systemically at P2 to P5 and a graph of the calculated vascular area. In this masked study, 50 mg/kg αApelinR decreased vascular growth by 29.8% (p<0.0001) compared to Fc treated controls. Retinal endothelial cells were stained with GS Lectin I. Images were taken at 20× (for quantification) and 40×. Statistical analysis was done with Student T-test. Selective inhibition of ApelinR via systemic injection delays normal vascular outgrowth in the developing retina in P5 pups.

Example 4

Figure 4A:
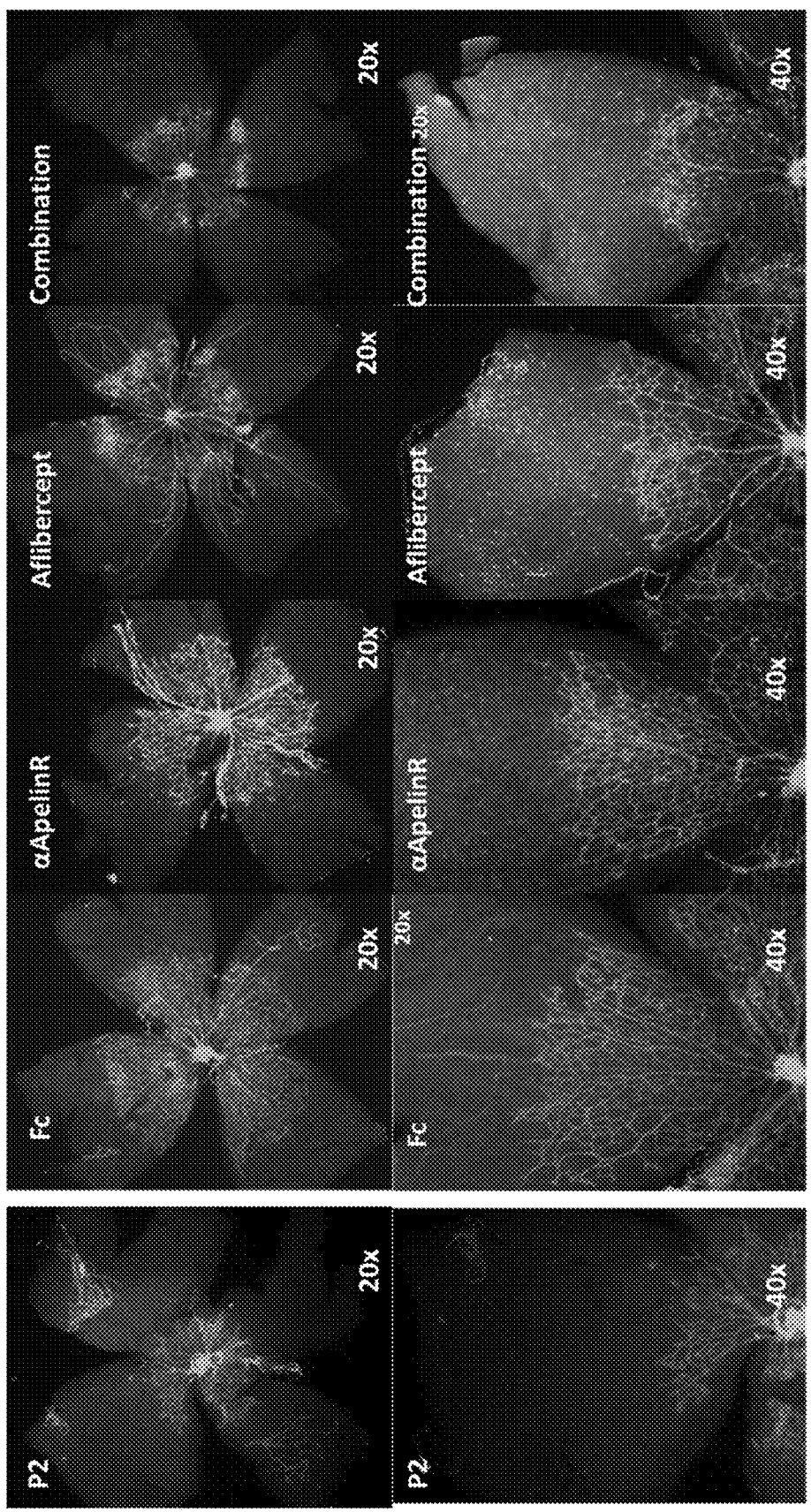
FIGS. 4A and 4B are representative photomicrographs of mouse retinas treated systemically (IP) at P2 to P5 and a graph of the calculated vascular area. Residual vascular area was significantly smaller in combination (αApelinR+aflibercept) (62% at 50 mg/kg, p<0.0001) compared to single reagents, αApelinR (31% at 50 mg/kg, p<0.001) or aflibercept (43% at 50 mg/kg, p<0.005) alone. Retinal endothelial cells were stained with GS Lectin I. Note the effects on dose and relational vascularized area. Images were taken at 20× (for quantification) and 40×. Statistical analysis was done with one-way ANOVA with post-hoc Tukey test. In both systemic and intravitreal (see FIGS. 5A and 5B) administration, αApelinR, and aflibercept combination therapy resulted in regression of normal developing retinal vasculature. Blocking both ApelinR and VEGFA via systemic injection is more effective in hindering vascular outgrowth compared to blocking ApelinR or VEGFA alone. In this model, combination treatment further decreased vascular area by 46% (p<0.0005) compared to αApelinR and 32% (p<0.001) compared to aflibercept.
Figure 4B:
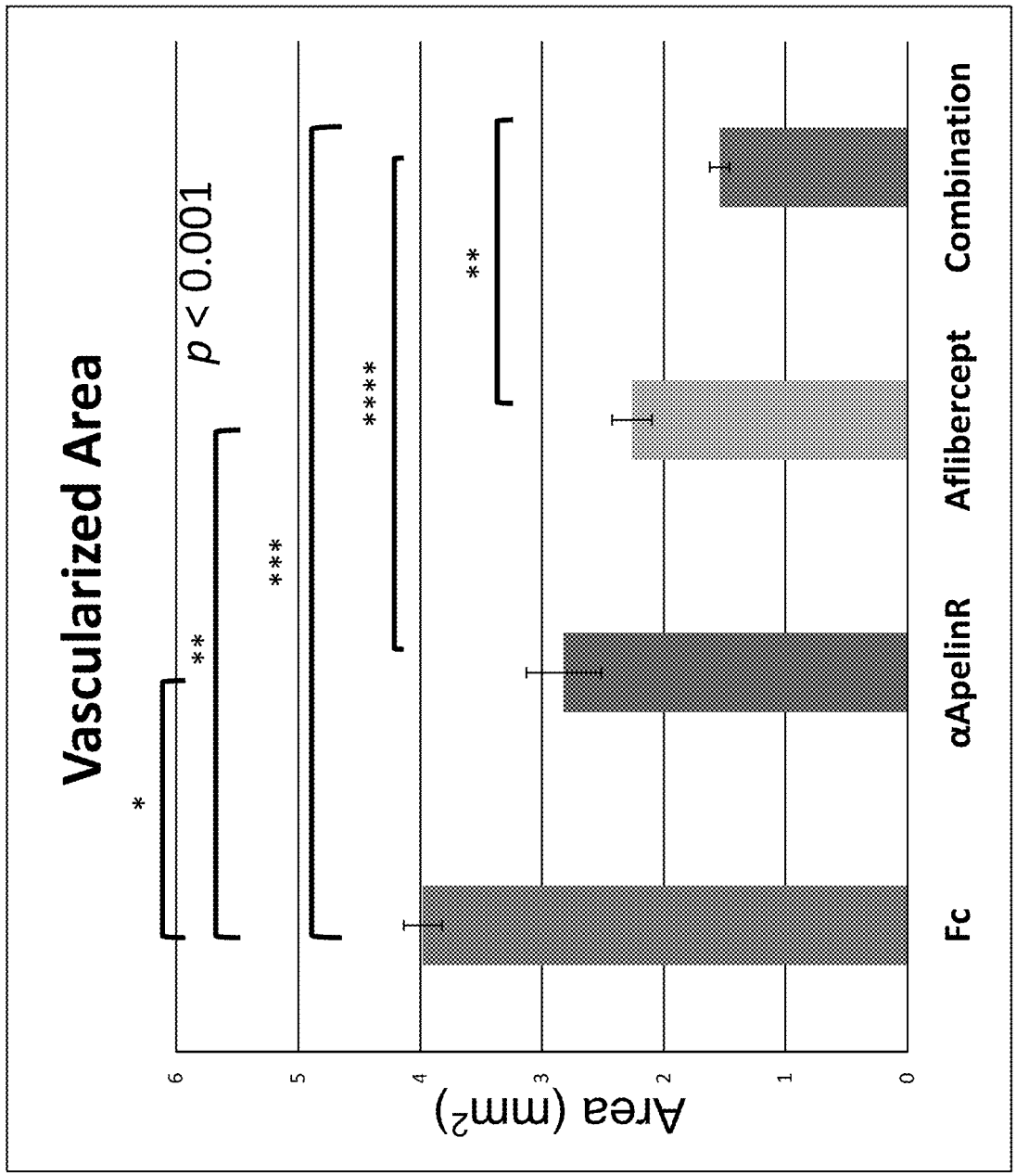

In another experiment in the RVD model (performed analogously to Example 1), P4 Hu pups were intravitreally (IVT) injected with 5 μg Fc, αAR or aflibercept or combination (αAR and aflibercept) and collected at P6. FIGS. 4A and 4B are representative photomicrographs of mouse retinas treated systemically at P2 to P5 and a graph of the calculated vascular area. Residual vascular area was significantly smaller in combination (αApelinR+aflibercept) (62% at 50 mg/kg, p<0.0001) compared to single reagents, αApelinR (31% at 50 mg/kg, p<0.001) or aflibercept (43% at 50 mg/kg, p<0.005) alone. Retinal endothelial cells were stained with GS Lectin I. Note the effects on dose and relational vascularized area. Images were taken at 20× (for quantification) and 40×. Statistical analysis was done with one-way ANOVA with post-hoc Tukey test. In both systemic and intravitreal (see Example 5 below) administration, αApelinR, and aflibercept combination therapy resulted in regression of normal developing retinal vasculature. Blocking both ApelinR and VEGFA via systemic injection is more effective in hindering vascular outgrowth compared to blocking ApelinR alone or VEGFA alone.

By injecting αAR at P2, vascular outgrowth was reduced by 23% (n=6 eyes/groups, p<0.05) at 25 mg/kg and 35% (n=6 eyes/group, p<0.005) at 50 mg/kg at P5. In our masked study were able to confirm our observations with a 29% (n=5 eyes per group, p<0.0001) decrease in vascular outgrowth compared to Fc controls.

Combined inhibition of ApelinR and VEGFA following IP and IVT injections, significantly limited vascular outgrowth by 62% at 50 mg/kg (n=4 eyes per group, p<0.0001) and 68% at 5 μg (n=4 eyes/group, p<0.0001). Aflibercept, alone produced 43% reduction at 50 mg/kg (n=4 eyes/group, p<0.001) and 65% reduction at 5 μg (n=3 eyes/group, p<0.005) in blood vessel outgrowth. Also, αAR, alone produced 31% reduction at 50 mg/kg (n=4 eyes/group p<0.001) and 43% reduction at 5 μg (n=4 eyes/group, p<0.005) in blood vessel outgrowth.

Example 5

Figure 5A:
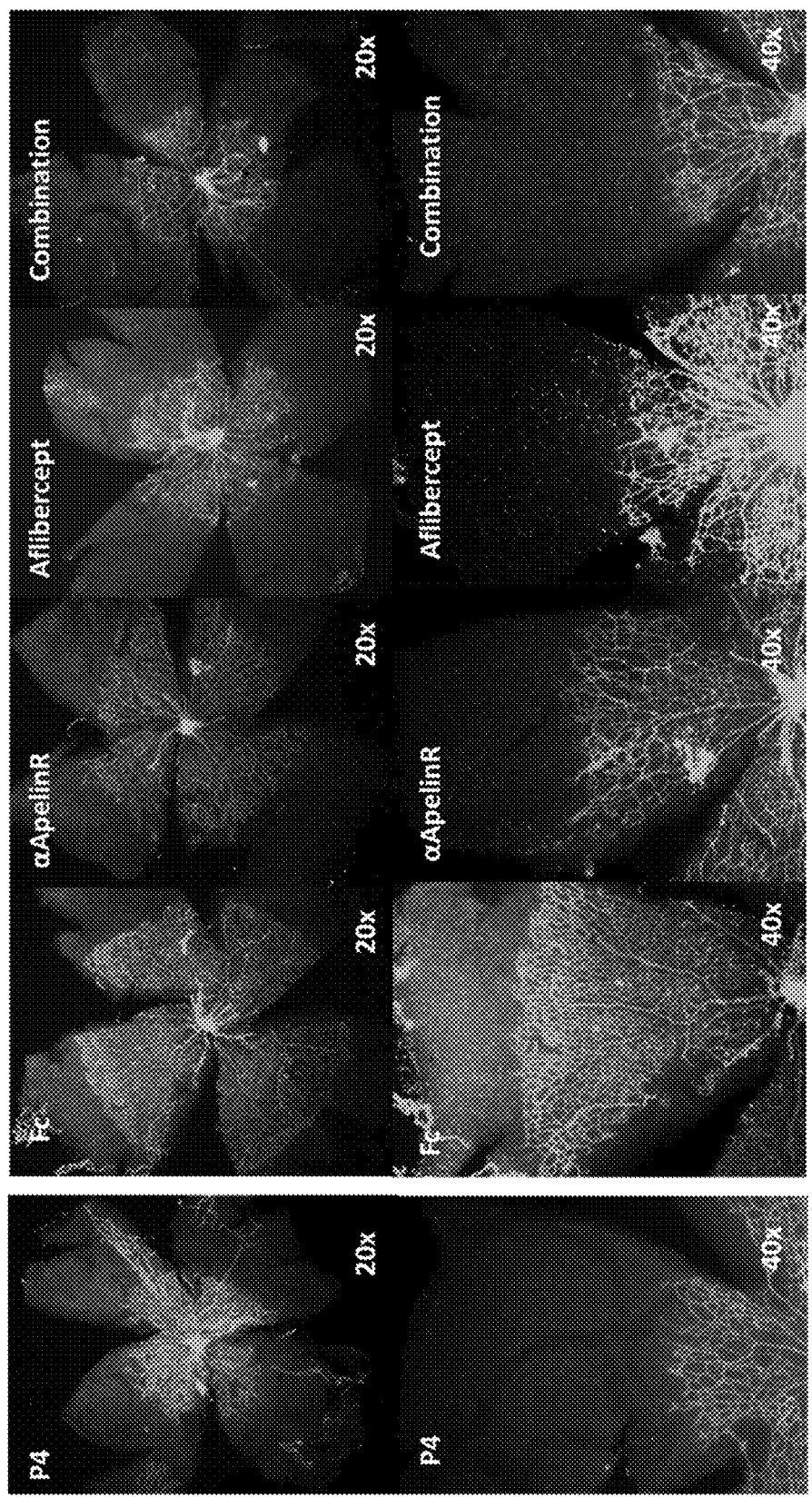
FIGS. 5A and 5B are representative photomicrographs of mouse retinas treated via intravitreal (IVT) injection at P4 to P6 and a graph of the calculated vascular area. Residual vascular area was significantly smaller in combination (αApelinR+aflibercept) (68% at 5 µg, p<0.0001) compared to single reagents, αApelinR (43% at 5 µg, p<0.0001) or aflibercept (65% at 5 µg, p<0.0001) alone. Retinal endothelial cells were stained with GS Lectin I. Note the effects on dose and relational vascularized area. Images were taken at 20× (for quantification) and 40×. Statistical analysis was done with one-way ANOVA with post-hoc Tukey test. In both systemic and intravitreal administration, αApelinR, and aflibercept combination therapy results in regression of normal developing retinal vasculature. Blocking both ApelinR and VEGFA via intravitreal injection is even more effective in hindering vascular outgrowth compared to blocking ApelinR and VEGFA alone. IVT combination treatment further decreased vascular area by 50% (p<0.0005) compared to αApelinR and 34% (p<0.001) compared to aflibercept.
Figure 5B:
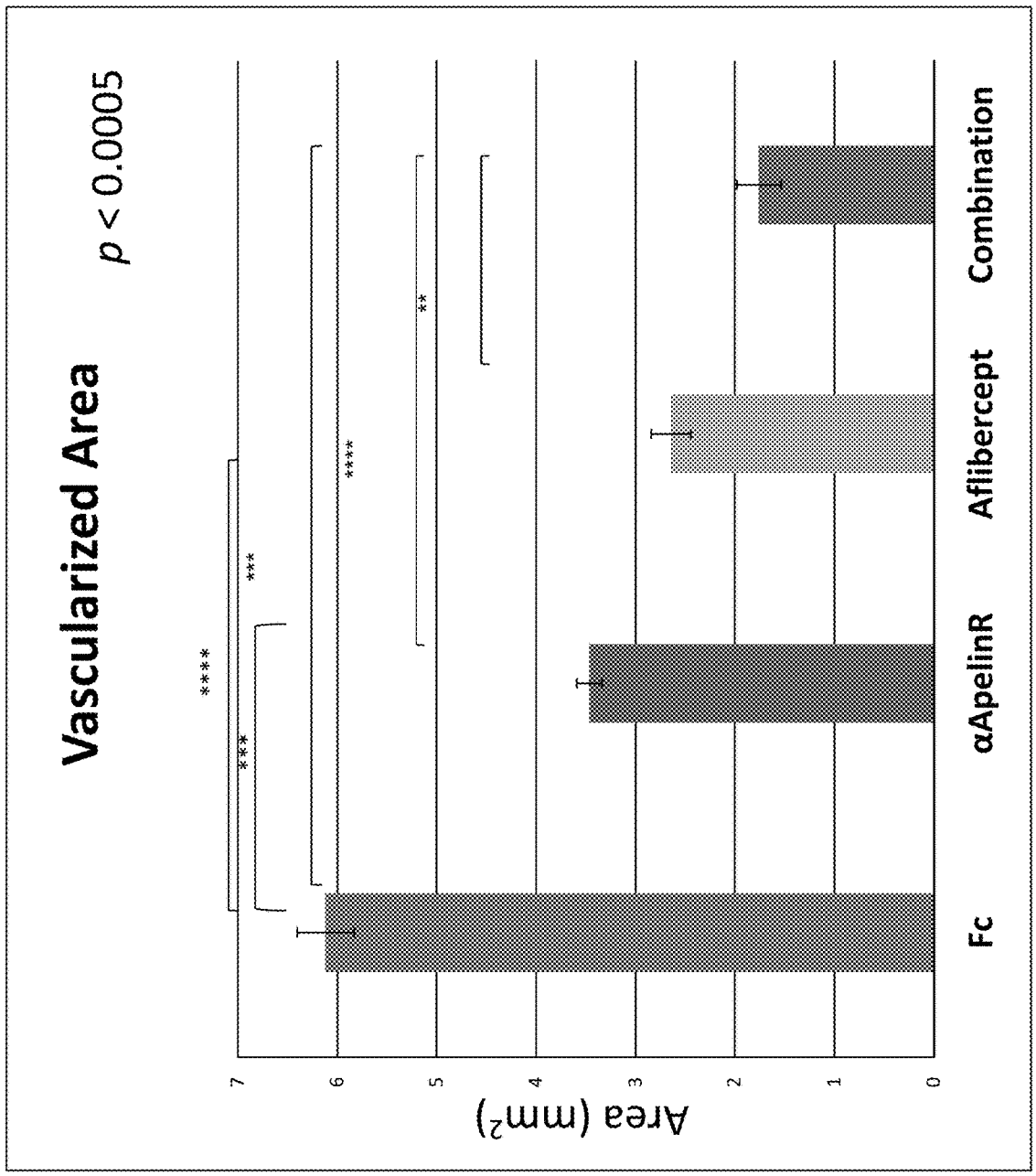

In another RVD experiment, mice were treated IVT with αApelinR (H2aM9232N) (5 μg), aflibercept (5 μg), or a combination (admixture) of αApelinR and aflibercept. FIGS. 5A and 5B are representative photomicrographs of mouse retinas treated intravitreally injected at P4 to P6 and a graph of the calculated vascular area. Residual vascular area was significantly smaller in combination (αApelinR+aflibercept) (68% at 5 μg, p<0.0001) compared to single reagents, αApelinR (43% at 5 μg, p<0.0001) or aflibercept (65% at 5 ug, p<0.0001) alone. Note the effects on dose and relational vascularized area. Images were taken at 20× (for quantification) and 40×. Statistical analysis was done with one-way ANOVA with post-hoc Tukey test. In both systemic and intravitreal administration, αApelinR, and aflibercept combination therapy results in regression of normal developing retinal vasculature. Blocking both ApelinR and VEGFA via intravitreal injection is even more effective in hindering vascular outgrowth compared to blocking ApelinR and VEGFA alone.

Example 6

The murine model of oxygen-induced ischemic retinopathy (OIR) is a well characterized model of pathological neovascularization associated with elevated expression of the essential pro-angiogenic factor, VEGF (Smith et al. 1994 Invest Ophthalmol Vis Sci 35:101-111; Neely et al. 1998 Am J. Pathol 153:665-670; Saint-Geniez et al. 2004 Int J Dev Biol 48:1045-1058) and thus relevant to pathological angiogenesis associated with diverse disease conditions (Ferrarra et al. 2005 Nature 438:967-974).

An investigation was undertaken to determine the effects of the anti-APLNR antibody on the growth of retinal vessel, formation of vascular abnormalities and retinal perfusion in oxygen-induced ischemic retinopathy (OIR).

To determine whether apelin/APLNR signaling plays a role in pathologic angiogenesis as well as during normal development, the OIR model was utilized. In the OIR model, exposure of mouse pups to hyperoxia at P6 results in a rapid obliteration of capillaries in the central retina. Following return to room air at P11, the avascular zone becomes severely hypoxic, which in turn elicits extensive abnormal neovascularization, characterized by the ectopic growth of vessels into the vitreous (epiretinal vascular 'tufts') and the formation of abnormal arteriovenous shunts; central parts of the retina remain largely avascular for an extended period.

C57/B16 mice (Taconic) were used to study the effect of VEGF trap or neutralizing APLNR antibody on retinal neovascularization in OIR. OIR was produced following the method developed by Smith et al. 1994 (supra). Briefly, humanized mouse pups were placed in a hyperoxic environment (75% $O_2$) at P6 and returned to room air at P11. Exposure to hyperoxia induces rapid vasoobliteration in the central retina. When mice are returned to room air (P11), the loss of vessels from the central retina results in severe hypoxia/ischemia which in turn stimulates the pathological vascular changes. Pups were injected systemically with 50 mg/kg Fc (control), αApelinR, or aflibercept at P12 and collected at P16. Retinal endothelial cells were stained with GS Lectin I.

Figure 6A:
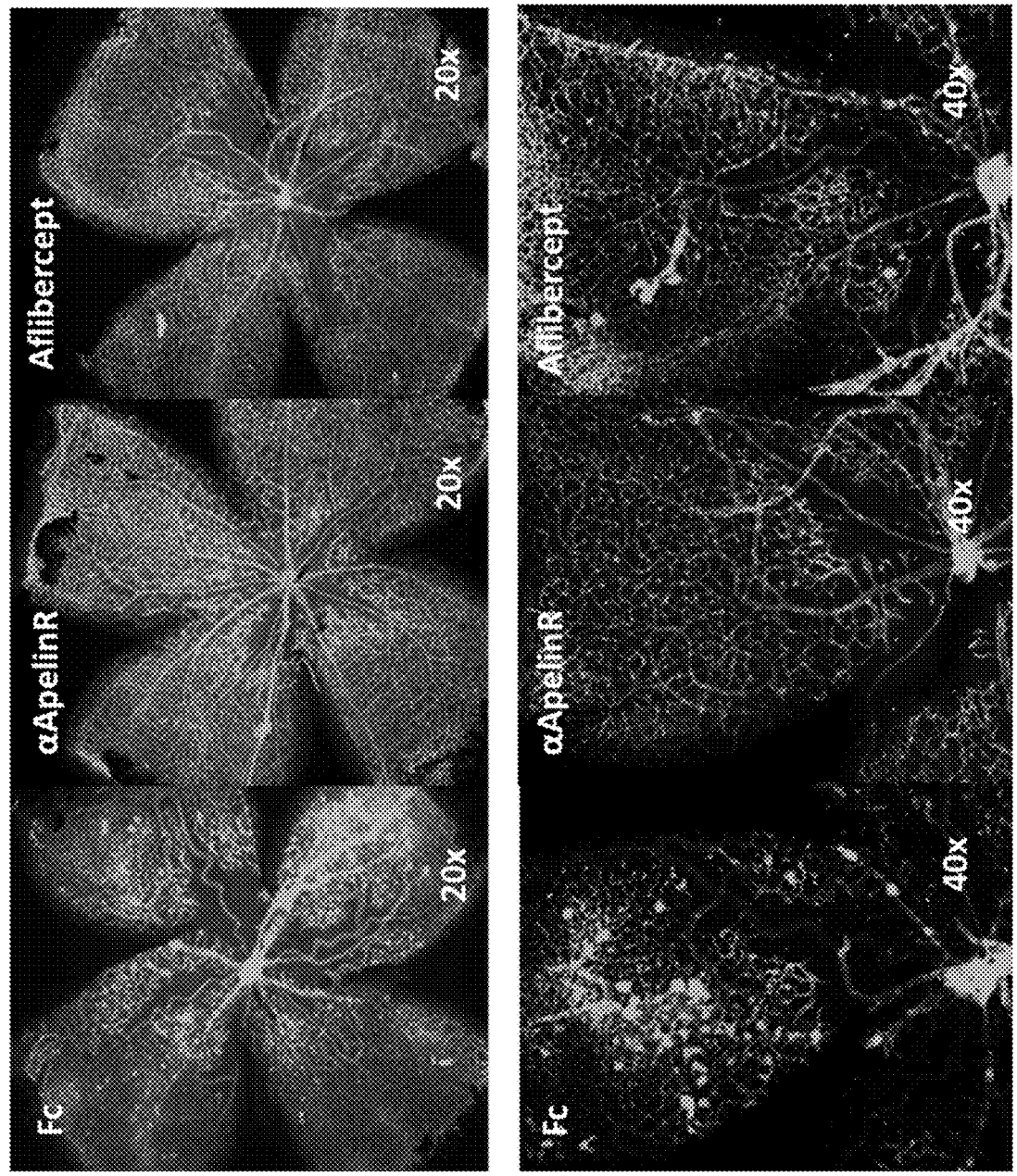
FIGS. 6A and 6B are representative photomicrographs of OIR mouse retinas treated systemically (IP) at P12 to P16 and graphs of the calculated avascular area. Residual avascular area was significantly smaller in αApelinR (29%, p<0.05) and aflibercept (27.5%, p<0.01) retinas compared to Fc (control) retinas. Notice the significant decrease in neovascular tufts in αApelinR (67%, p<0.0001) and aflibercept (94%, p<0.0005) treated samples compared to Fc. Retinal endothelial cells were stained with GS Lectin I. Images were taken at 20× (Avascular area quantification) and 40× (Abnormal neovascular area quantification). Statistical analysis was done with Student T-test. ApelinR and VEGFA inhibition via systemic injection both promote retinal vascular regrowth and reduces abnormal neovascularizations.
Figure 6B:
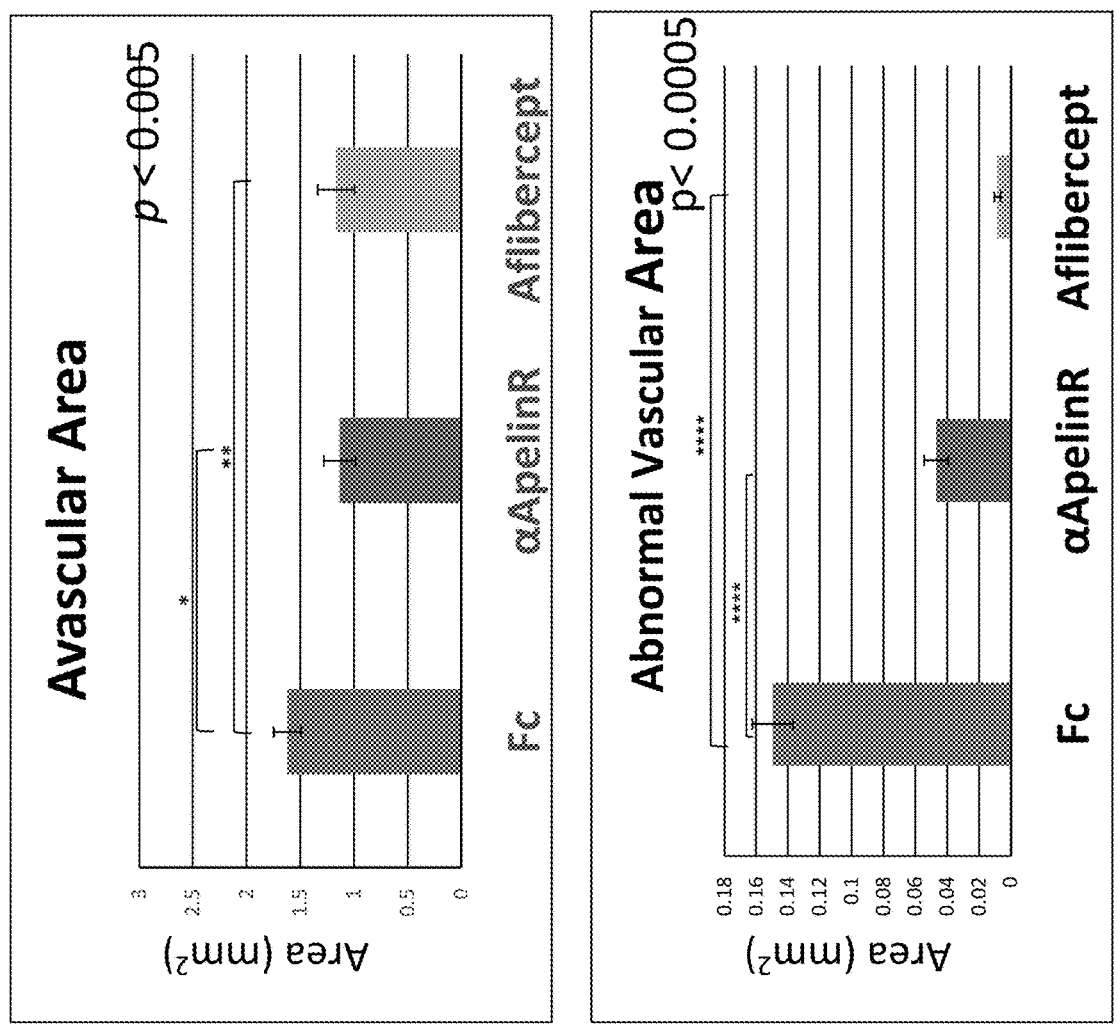

FIGS. 6A and 6B are representative photomicrographs of OIR mouse retinas treated systemically at P12 to P16 and graphs of the calculated avascular area. Residual avascular area was significantly smaller in αApelinR (29%, p<0.05) and aflibercept (27.5%, p<0.01) retinas compared to Fc (control) retinas. Notice the significant decrease in neovascular tufts in αApelinR (67%, p<0.0001) and aflibercept (94%, p<0.0005) treated samples compared to Fc. Retinal endothelial cells were stained with GS Lectin I. Images were taken at 20× (Avascular area quantification) and 40× (Abnormal neovascular area quantification). Statistical analysis was done with one-way ANOVA with post-hoc Tukey test. In both systemic and intravitreal administration, selective inhibition of ApelinR promotes retinal vascular regrowth and reduces neovascularizations in OIR mice. ApelinR and VEGFA inhibition via systemic injection promotes retinal vascular regrowth and reduces abnormal neovascularizations.

Figure 7A:
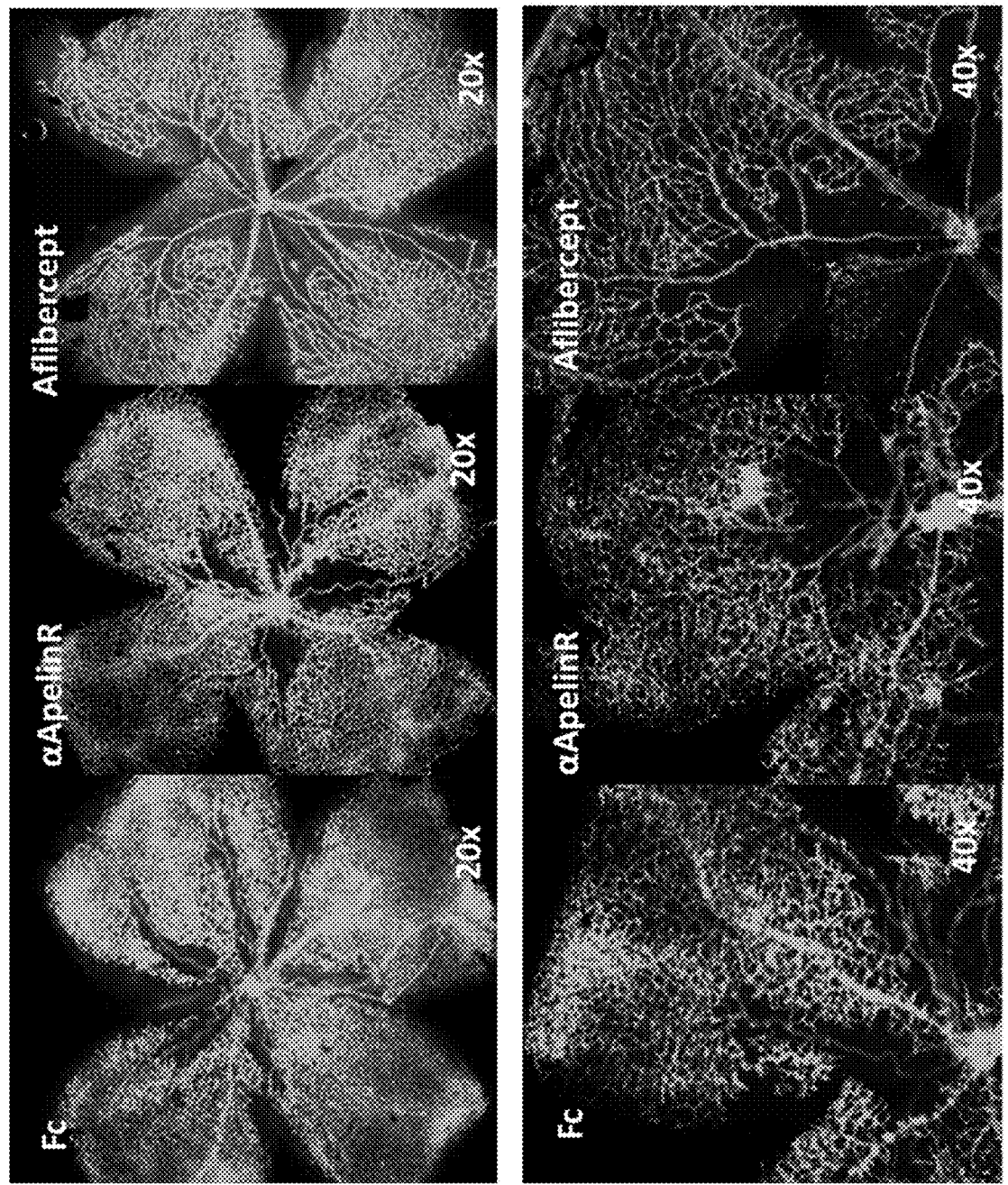
FIGS. 7A and 7B are representative photomicrographs of oxygen induced retinopathy (OIR) mouse retinas treated intravitreally at P12 to P16, and graphs of calculated avascular area. Residual avascular area was significantly decreased in αApelinR (27.5% p<0.05) and increased in aflibercept (32%, p<0.0001) conditions compared to Fc controls. Notice the significant decrease in neovascular tufts in αApelinR (60%, p<0.0001) and complete disappearance of tufts in aflibercept samples. Retinal endothelial cells were stained with GS Lectin I. Note the effects on dose and relational vascularized area. Images were taken at 20× (Avascular area quantification) and 40× (Abnormal neovascular area quantification). Statistical analysis was done with one-way ANOVA with post-hoc Tukey test. In both systemic (see FIGS. 6A and 6B) and intravitreal administration, selective inhibition of ApelinR promotes retinal vascular regrowth and reduces neovascularizations in OIR mice. ApelinR inhibition via intravitreal injection improves vascular regrowth and decreases abnormal neovascularizations, while VEGFA inhibition arrests vascular regrowth and completely halts any neovascularizations.
Figure 7B:
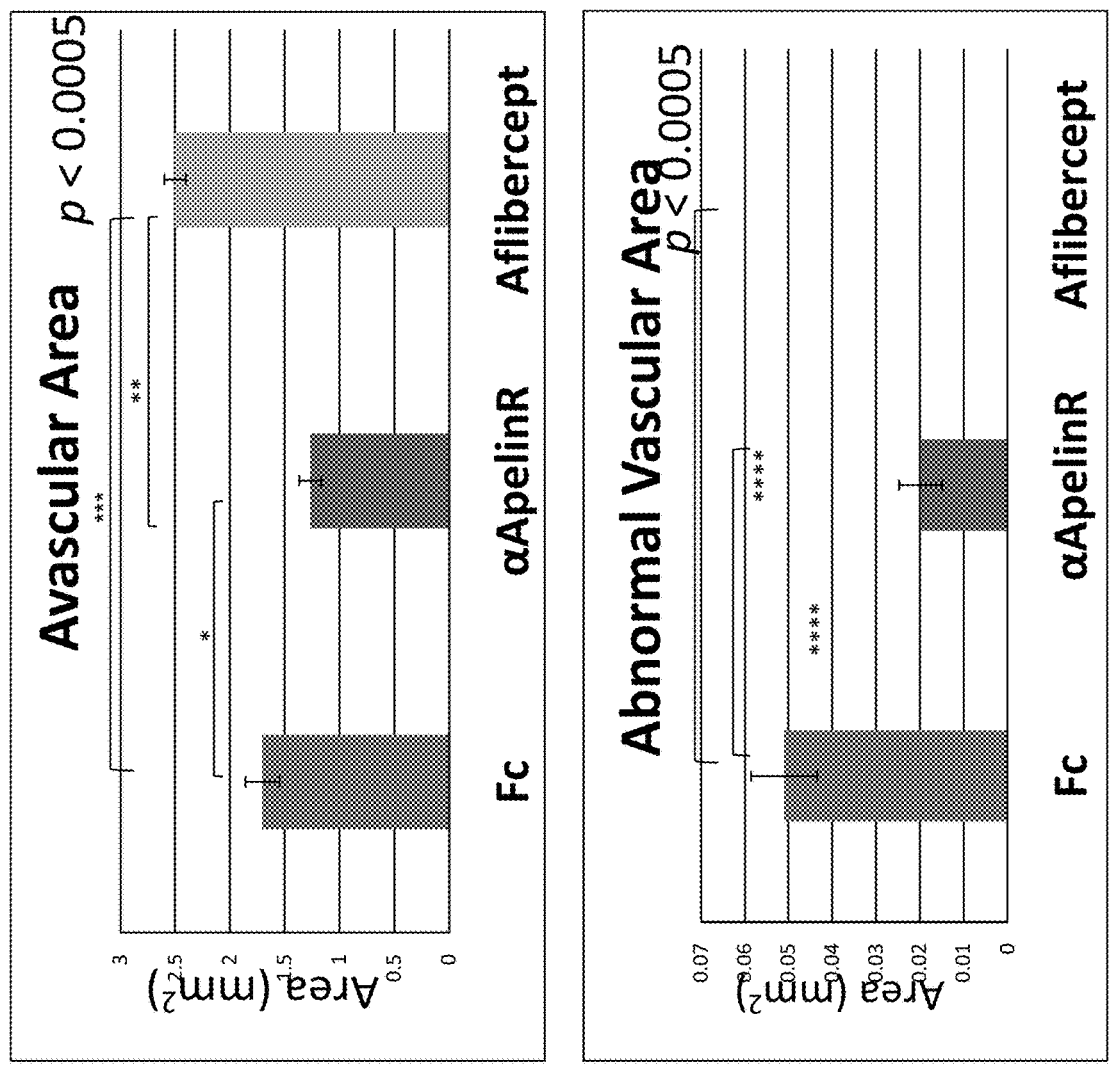

OIR mice were treated analogously to the above investigation, except OIR mice were injected IVT with 5 µg Fc, αAR, or aflibercept at P12 and collected at P16. FIGS. 7A and 7B are representative photomicrographs of OIR mouse retinas treated intravitreally at P12 to P16 and graphs of calculated avascular area. Avascular area was significantly decreased in αApelinR (27.5% p<0.05) and increased in aflibercept (32%, p<0.0001) conditions compared to Fc controls. Notice the significant decrease in neovascular tufts in αApelinR (60%, p<0.0001) and complete disappearance of tufts in aflibercept samples. Retinal endothelial cells were stained with GS Lectin I. Images were taken at 20× (Avascular area quantification) and 40× (Abnormal neovascular area quantification). Statistical analysis was done with one-way ANOVA with post-hoc Tukey test. In both systemic and intravitreal administration, selective inhibition of ApelinR promotes retinal vascular regrowth and reduces neovascularizations in OIR mice. ApelinR inhibition via intravitreal injection improves vascular regrowth and decreases abnormal neovascularizations, while VEGFA inhibition arrests vascular regrowth and completely halts any neovascularizations.

In the OIR model, αAR and aflibercept were able to promote vessel regrowth. When pups were IP injected at OIR P12, αAR and aflibercept significantly reduced avascular areas by 29% and 27% (n=6 eyes/group, p<0.05) and neovascularizations by 69% and 94% (n=6 eyes/group, p<0.0001) at P16 respectively. With IVT administration aflibercept reduced vessel regrowth by 30% (n=4 eyes/group, p<0.0001) and eliminated all neovascularization, while αAR was able to promote vessel regrowth by 30% (n=4 eyes/group, p<0.05) and reduce neovascularizations by 60% (n=4 eyes/group, p<0.0001).

A combination of APLNR antagonist and VEGF trap, e.g. aflibercept, also regressed pathological angiogenesis and promoted normal vascular regrowth in an OIR model, as discussed in Example 7. This combination is therefore expected to treat pathological angiogenesis as seen in various eye diseases, including retinopathy of prematurity.

Example 7

In a further in vivo experiment, the OIR model, as discussed above in Example 6, was used to evaluate the organization and density of revascularization. Briefly, humanized mouse pups were placed in a hyperoxic environment (75% $O_2$) at P6 and returned to room air at P11. Exposure to hyperoxia induces rapid vasoobliteration in the central retina. When mice are returned to room air (P11), the loss of vessels from the central retina results in severe hypoxia/ischemia which in turn stimulates the pathological vascular changes. Pups were injected systemically with 50 mg/kg Fc (control), αAPLNR (H4H9232N), or aflibercept (VEGF-Trap), or 25 mg/kg of a combination of αAPLNR and aflibercept at P12 and collected at P16. Retinal endothelial cells were stained with GS Lectin I.

Figure 8B:
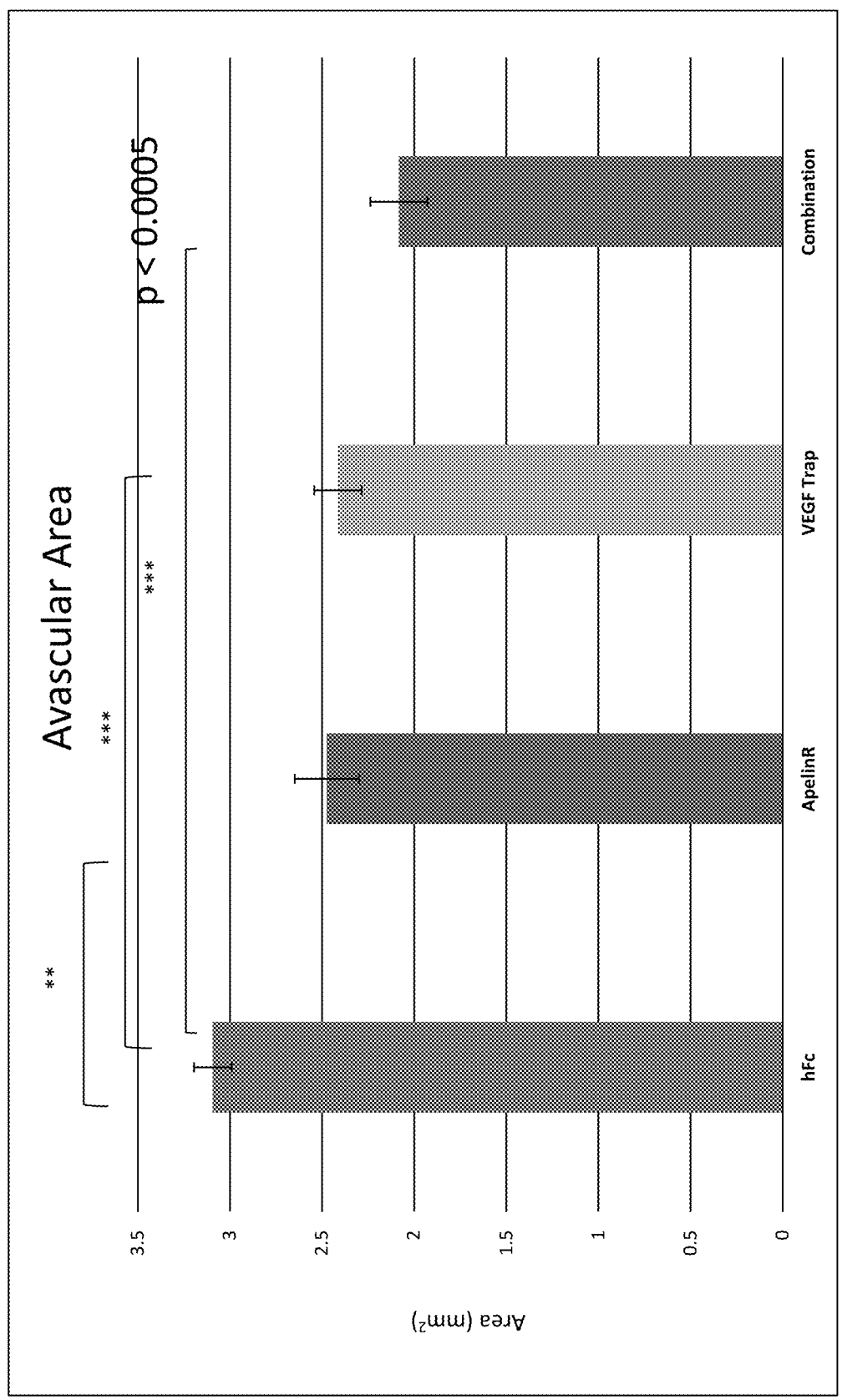

FIGS. 8A and 8B are representative photomicrographs (20×) of OIR mouse retinas treated systemically at P12 to P16 and graphs of the calculated avascular area. The rate of regrowth with the combination treatment is similar to each agent alone, and to that end, vascular regrowth is improved in all treatment conditions compared to hFc-treated control retinas, with combination treatment showing a slightly more decreased average avascular area. FIG. 8B shows that there were significant changes in avascular area between treatment groups (p<0.0005). Vessel area was significantly decreased with anti-APLNR antibody (, p<0.05), with VEGF Trap (*, p<0.005), and with the combination (***, p<0.05) compared to Fc control. Statistical analysis was done with One-way ANOVA with post-hoc Tukey test.

Figure 9A:
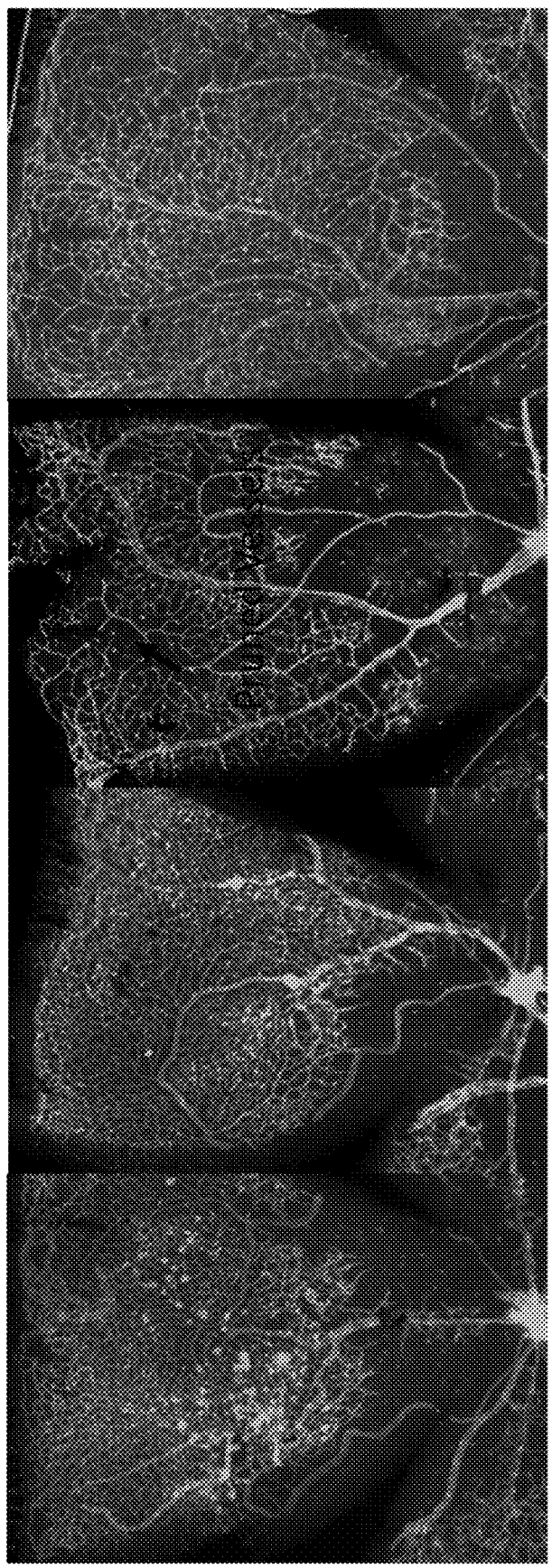
FIGS. 9A and 9B are representative photomicrographs (40×) of OIR mouse retinas treated systemically at P12 to P16 and graphs of the calculated abnormal vascular area. The combination treatment shows fewer pruned vessels compared to aflibercept, and fewer abnormal neovascularizations compared to anti-APLNR and Fc control (FIG. 9A).
Figure 9B:
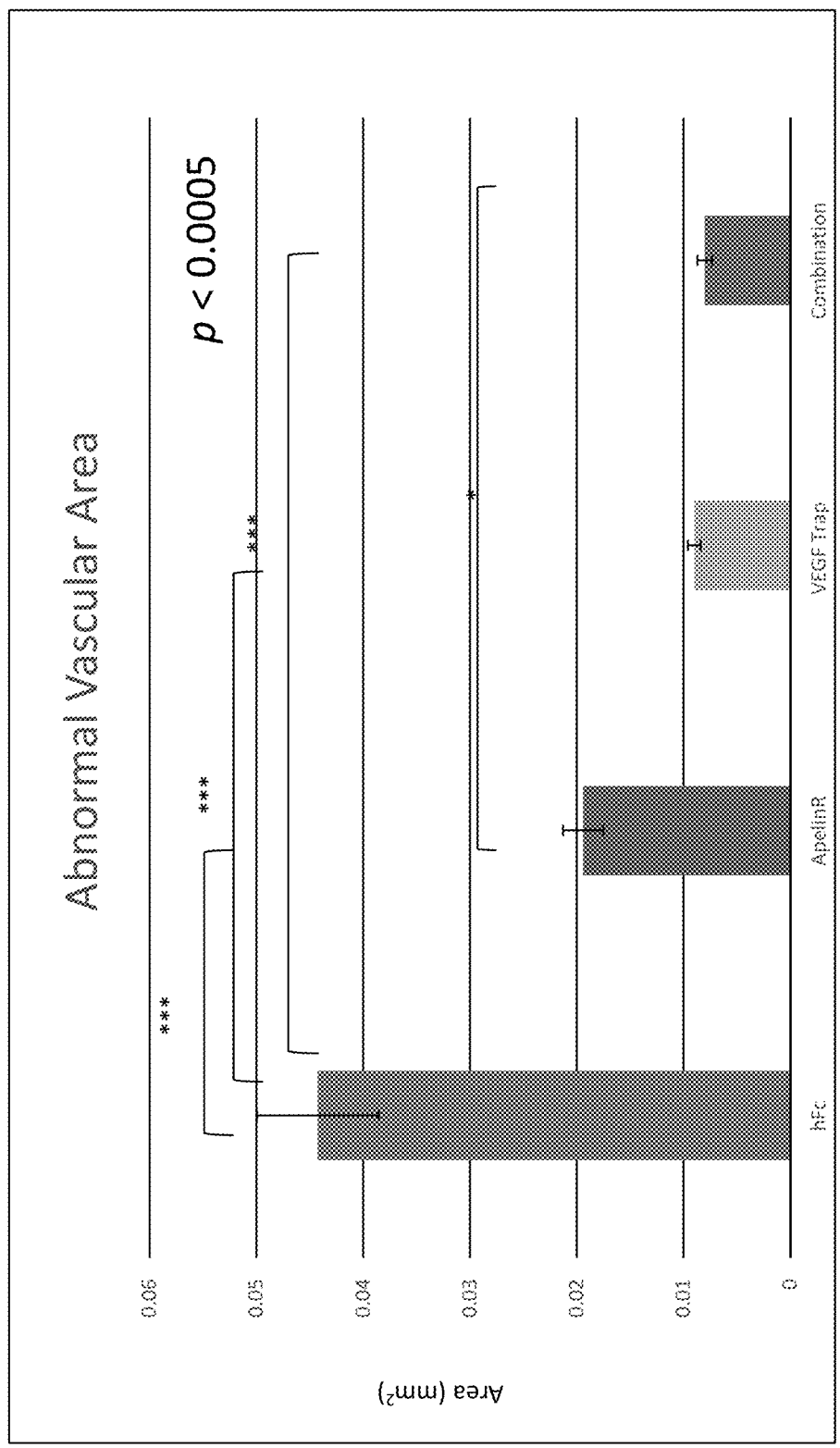

FIGS. 9A and 9B are representative photomicrographs (40×) of OIR mouse retinas treated systemically at P12 to P16 and graphs of the calculated abnormal vascular area. The combination treatment shows fewer pruned vessels compared to VEGF Trap, and fewer abnormal neovascularizations compared to anti-APLNR and Fc control (FIG. 9A). FIG. 9B shows that there were significant changes in abnormal vascular area between treatment groups (p<0.0005). Abnormal vascular area was significantly decreased with anti-APLNR (*, p<0.0005), with VEGF Trap (* p<0.005), and with the combination (***, p<0.0005) compared to Fc control. The abnormal vascular area was also significantly decreased in the combination treatment group (*, p<0.05) compared to the anti-APLNR treatment group. Statistical analysis was done with One-way ANOVA with post-hoc Tukey test.

Figure 10:
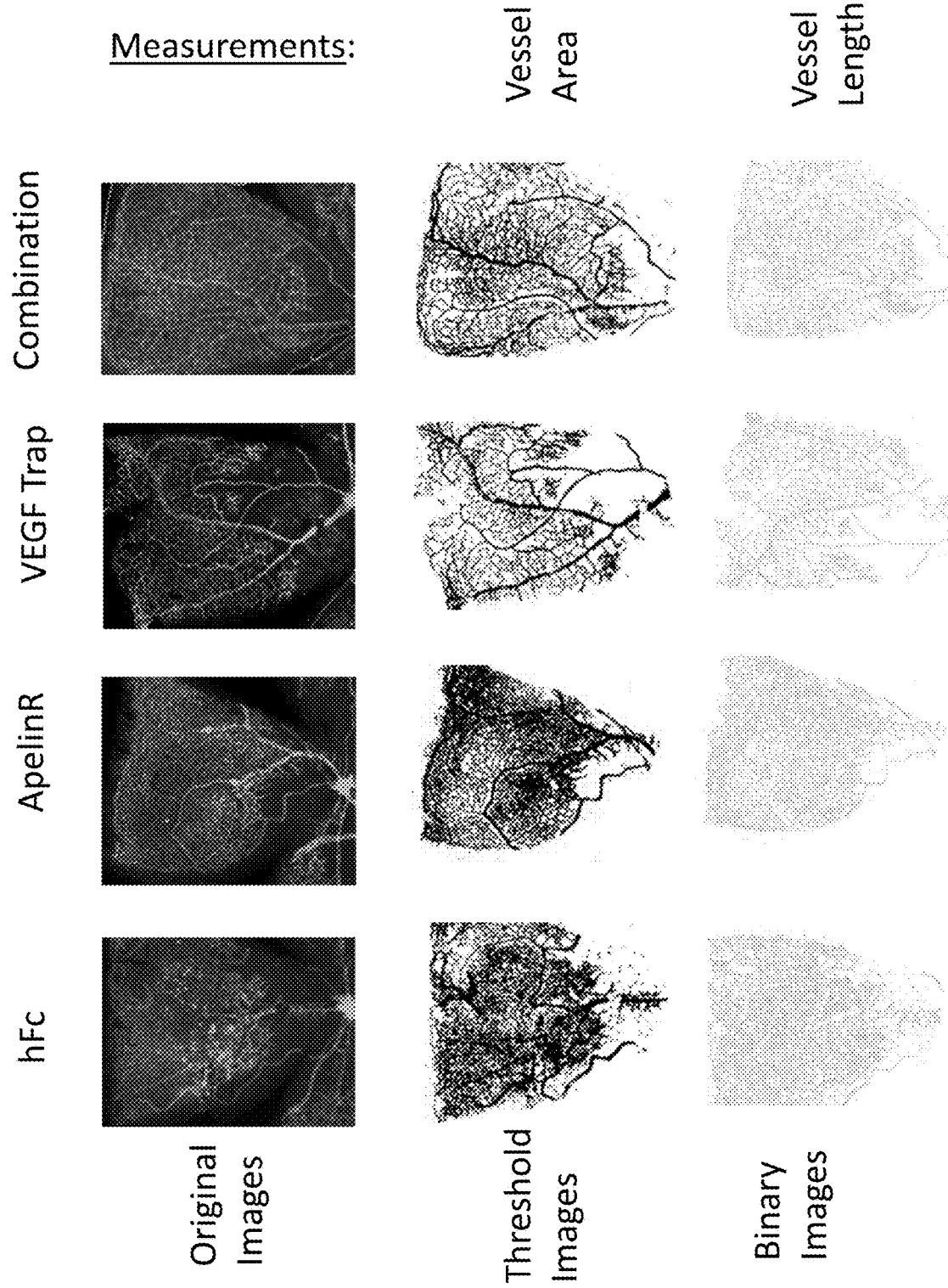
FIG. 10 is representative of the image processing and measurement techniques used to calculate vessel area and vessel length in Example 7. The "original images" are the 40× photomicrographs shown in FIG. 9A.

FIG. 10 is representative of the image processing and measurement techniques used to calculate vessel area and vessel length. The "original images" are the 40× photomicrographs shown in FIG. 9A. The "threshold images" and the "binary images" are discussed more specifically in connection with FIGS. 11A, 11B, 12A and 12B, below.

Figure 11A:
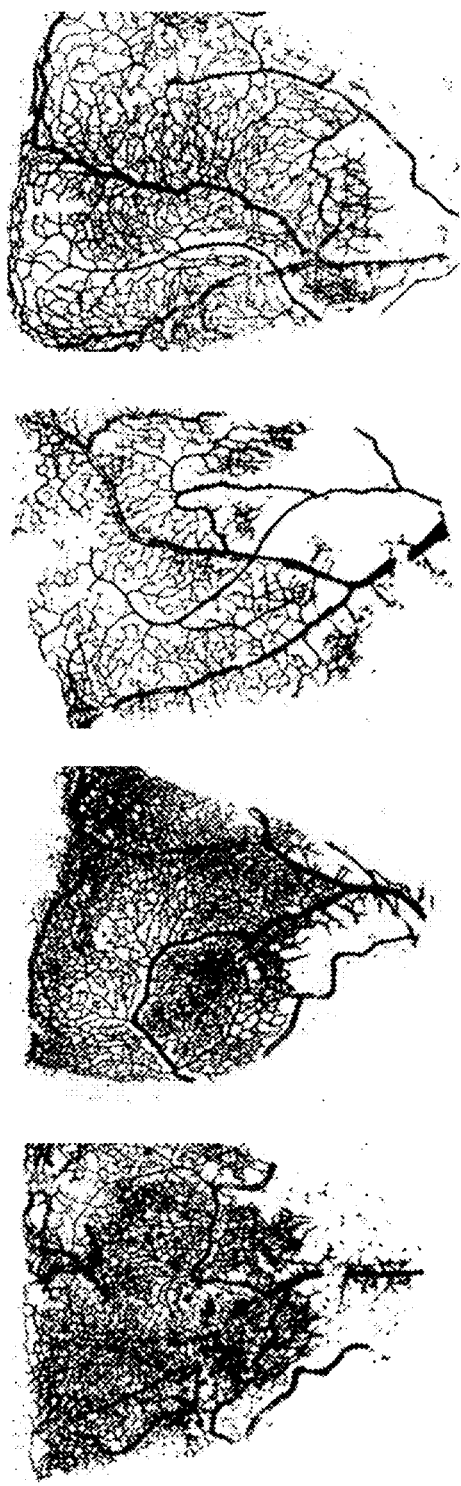
FIGS. 11A and 11B are representative processed images showing the organization and uniformity of vessels from the photomicrographs (40×) of OIR mouse retinas treated systemically at P12 to P16 and graphs of the calculated vessel area.
Figure 11B:
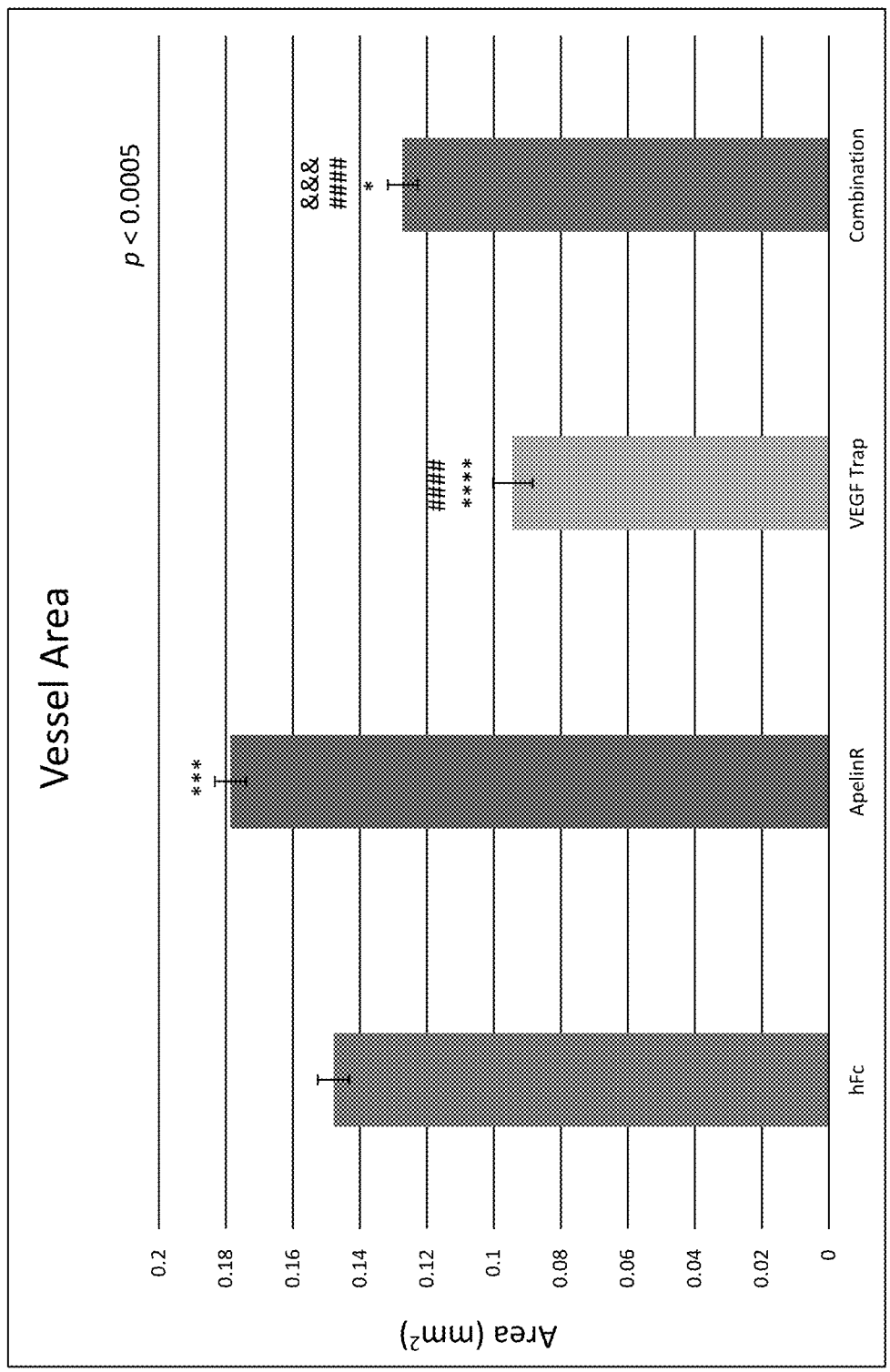

FIGS. 11A and 11B are representative processed images showing the organization and uniformity of vessels from the photomicrographs (40×) of OIR mouse retinas treated systemically at P12 to P16 and graphs of the calculated vessel area. As shown in FIG. 11A, the combination of anti-APLNR antibody and VEGF Trap produced retinal vessels that are more organized and uniform compared to anti-APLNR alone, and less sparse (with fewer pruned vessels) compared to VEGF Trap alone. FIG. 11B shows that there were significant changes in vessel area between the treatment groups (p<0.0005). Vessel area was significantly increased with anti-APLNR (*, p<0.0005) and decreased with VEGF Trap (*, p<0.005) and the combination treatment (*, p<0.05) compared to Fc control. Vessel area was significantly decreased with VEGF Trap (####, p<0.0005) and with the combination (####, p<0.0005) compared to anti-APLNR. In contrast, vessel area was significantly increased with the combination treatment (&&&, p<0.005) compared to VEGF Trap. Statistical analysis was done with One-way ANOVA with post-hoc Tukey test.

Figure 12A:
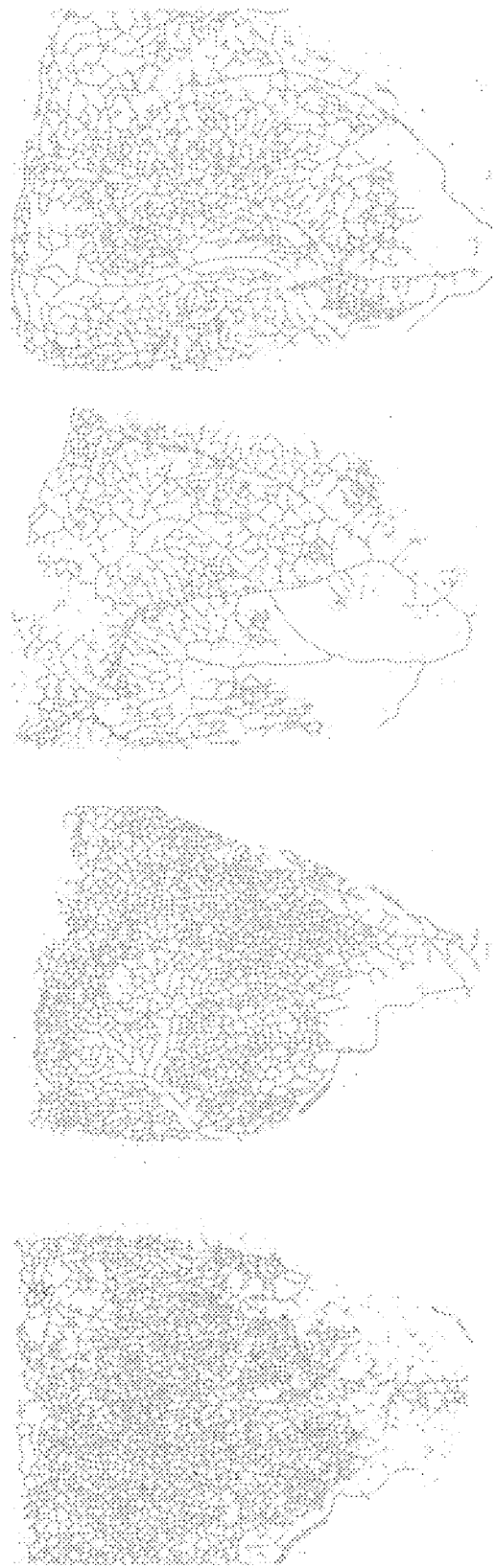
FIGS. 12A and 12B are representative processed images showing the density of vessels from the photomicrographs (40×) of OIR mouse retinas treated systemically at P12 to P16 and graphs of the calculated vessel length.
Figure 12B:
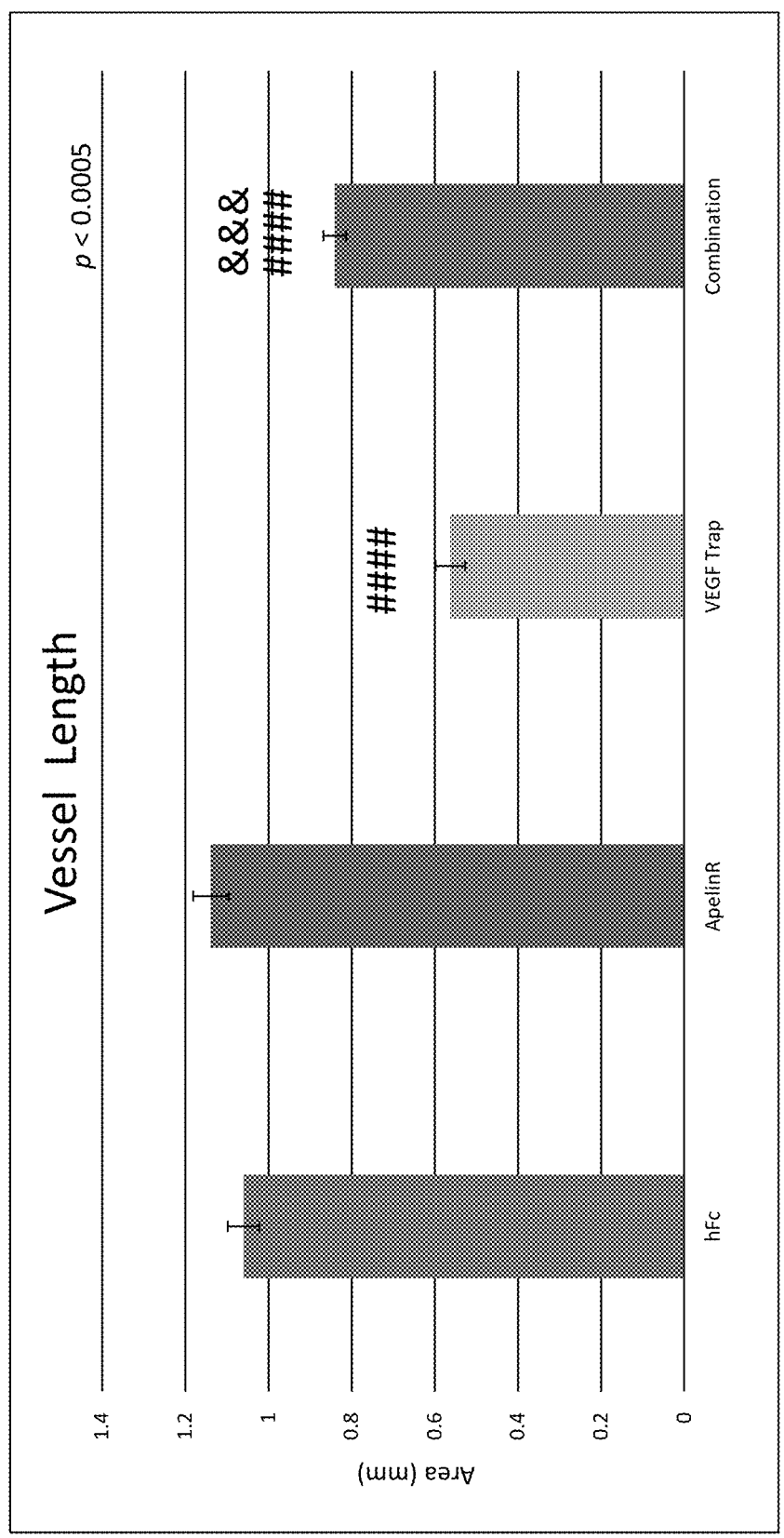

FIGS. 12A and 12B are representative processed images showing the density of vessels from the photomicrographs (40×) of OIR mouse retinas treated systemically at P12 to P16 and graphs of the calculated vessel length. As shown in FIG. 12A, the combination of anti-APLNR antibody and VEGF Trap produced retinal vessels of intermediate density compared to anti-APLNR (greater density) or VEGF Trap (lesser density) alone. FIG. 12B shows that there were significant changes in vessel length between the treatment groups (p<0.0005). Vessel length was significantly decreased with VEGF Trap (####, p<0.0005) and with the combination (####, p<0.0005) compared to anti-APLNR. In contrast, vessel length was significantly increased with the combination treatment (&&&, p<0.005) compared to VEGF Trap. Statistical analysis was done with One-way ANOVA with post-hoc Tukey test.

As shown in FIGS. 8A-12B, and discussed above, the combination of an anti-APLNR antibody and a VEGF Trap promotes revascularization, leading to a decrease in avascular area compared to Fc controls. In addition, the combination treatment inhibits pathological neovascularization, and produces an intermediate effect on vessel area and vessel length, compared to anti-APLNR antibody or VEGF Trap treatments alone In particular, the combination treatment promotes microvessel growth between the major blood vessels compared to VEGF Trap treatment, and improves blood vessel organization and uniformity compared to anti-APLNR antibody treatment.

The present disclosure is not to be limited in scope by the specific embodiments described herein. Indeed, various modifications of the disclosure in addition to those described herein will become apparent to those skilled in the art from the foregoing description and the accompanying figures. Such modifications are intended to fall within the scope of the appended claims.

What is claimed is:

1. A method for treating a vascular eye disease or disorder, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and
   administering a therapeutically effective amount of a vascular endothelial growth factor (VEGF) antagonist, to the subject.

2. The method of claim 1, wherein the eye disease or disorder is selected from the group consisting of diabetic retinopathy, proliferative diabetic retinopathy, diabetic macular edema, age-related macular degeneration, retinal neovascularization, central retinal vein occlusion, branched retinal vein occlusion, polypoidal choroidal vasculopathy, choroidal neovascularization (CNV), degenerative myopia (myopic CNV), neovascular glaucoma, and retinopathy of prematurity.

3. The method of claim 2, wherein the eye disease or disorder is age-related macular degeneration.

4. The method of claim 2, wherein the eye disease or disorder is diabetic macular edema.

5. The method of claim 1, wherein the antibody or antigen-binding fragment comprises a HCVR/LCVR amino acid sequence pair selected from the group consisting of: SEQ ID NOs: 2/7 and 13/18.

6. The method of claim 1, wherein the VEGF antagonist comprises a VEGF receptor-based chimeric molecule (VEGF Trap).

7. The method of claim 6, wherein the VEGF Trap is aflibercept.

8. A method for inhibiting retinal angiogenesis, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and
   administering a therapeutically effective amount of a vascular endothelial growth factor (VEGF) antagonist, to the subject.

9. The method of claim 8, wherein the subject has been diagnosed with an eye disease or disorder selected from the group consisting of diabetic retinopathy, proliferative diabetic retinopathy, diabetic macular edema, age-related macular degeneration, retinal neovascularization, central retinal vein occlusion, branched retinal vein occlusion, polypoidal choroidal vasculopathy, choroidal neovascularization (CNV), degenerative myopia (myopic CNV), neovascular glaucoma, and retinopathy of prematurity.

10. The method of claim 9, wherein the eye disease or disorder is age-related macular degeneration.

11. The method of claim 9, wherein the eye disease or disorder is diabetic macular edema.

12. The method of claim 8, wherein the antibody or antigen-binding fragment comprises a HCVR/LCVR amino acid sequence pair selected from the group consisting of: SEQ ID NOs: 2/7 and 13/18.

13. The method of claim 8, wherein the VEGF antagonist comprises a VEGF receptor-based chimeric molecule (VEGF Trap).

14. The method of claim 13, wherein the VEGF Trap is aflibercept.

15. A method of inhibiting retinal neovascularization, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and
   administering a therapeutically effective amount of a vascular endothelial growth factor (VEGF) antagonist, to the subject.

16. The method of claim 15, wherein the antibody or antigen-binding fragment comprises a HCVR/LCVR amino acid sequence pair selected from the group consisting of: SEQ ID NOs: 2/7 and 13/18.

17. The method of claim 15, wherein the VEGF antagonist comprises a VEGF receptor-based chimeric molecule (VEGF Trap).

18. The method of claim 17, wherein the VEGF Trap is aflibercept.

19. A method for inhibiting choroidal neovascularization, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and
   administering a therapeutically effective amount of a vascular endothelial growth factor (VEGF) antagonist, to the subject.

20. The method of claim 19, wherein the antibody or antigen-binding fragment comprises a HCVR/LCVR amino acid sequence pair selected from the group consisting of: SEQ ID NOs: 2/7 and 13/18.

21. The method of claim 19, wherein the VEGF antagonist comprises a VEGF receptor-based chimeric molecule (VEGF Trap).

22. The method of claim 21, wherein the VEGF Trap is aflibercept.

23. A method for improving vascular regrowth and decreasing abnormal neovascularizations, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and
   administering a therapeutically effective amount of a vascular endothelial growth factor (VEGF) antagonist, to the subject.

24. The method of claim 23, wherein the antibody or antigen-binding fragment comprises a HCVR/LCVR amino acid sequence pair selected from the group consisting of: SEQ ID NOs: 2/7 and 13/18.

25. The method of claim 23, wherein the VEGF antagonist comprises a VEGF receptor-based chimeric molecule (VEGF Trap).

26. The method of claim 25, wherein the VEGF Trap is aflibercept.

27. A method for promoting revascularization of a retina, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and
   administering a therapeutically effective amount of a vascular endothelial growth factor (VEGF) antagonist, to the subject.

28. The method of claim 27, wherein the antibody or antigen-binding fragment comprises a HCVR/LCVR amino acid sequence pair selected from the group consisting of: SEQ ID NOs: 2/7 and 13/18.

29. The method of claim 27, wherein the VEGF antagonist comprises a VEGF receptor-based chimeric molecule (VEGF Trap).

30. The method of claim 29, wherein the VEGF Trap is aflibercept.

31. A method for promoting uniform regrowth of retinal vessels, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and
   administering a therapeutically effective amount of a vascular endothelial growth factor (VEGF) antagonist, to the subject.

32. The method of claim 31, wherein the antibody or antigen-binding fragment comprises a HCVR/LCVR amino acid sequence pair selected from the group consisting of: SEQ ID NOs: 2/7 and 13/18.

33. The method of claim 31, wherein the VEGF antagonist comprises a VEGF receptor-based chimeric molecule (VEGF Trap).

34. The method of claim 33, wherein the VEGF Trap is aflibercept.

35. A method of improving vessel outgrowth in a retina, comprising:
   administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and administering a therapeutically effective amount of a vascular endothelial growth factor (VEGF) antagonist, to the subject.

36. The method of claim 35, wherein the antibody or antigen-binding fragment comprises a HCVR/LCVR amino acid sequence pair selected from the group consisting of: SEQ ID NOs: 2/7 and 13/18.

37. The method of claim 35, wherein the VEGF antagonist comprises a VEGF receptor-based chimeric molecule (VEGF Trap).

38. The method of claim 37, wherein the VEGF Trap is aflibercept.

39. A method for promoting uniform blood vessel growth in a retina, comprising:

administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and administering a therapeutically effective amount of a vascular endothelial growth factor (VEGF) antagonist, to the subject.

40. The method of claim 39, wherein the antibody or antigen-binding fragment comprises a HCVR/LCVR amino acid sequence pair selected from the group consisting of: SEQ ID NOs: 2/7 and 13/18.

41. The method of claim 39, wherein the VEGF antagonist comprises a VEGF receptor-based chimeric molecule (VEGF Trap).

42. The method of claim 41, wherein the VEGF Trap is aflibercept.

43. A method for improving blood vessel organization of a retina, comprising:

administering a therapeutically effective amount of an apelin receptor (APLNR) antagonist to a subject in need thereof, wherein the APLNR antagonist comprises an anti-APLNR antibody or antigen binding fragment thereof that specifically binds human APLNR, and wherein the antibody or antigen-binding fragment comprises HCDR1-HCDR2-HCDR3-LCDR1-LCDR2-LCDR3 domains, respectively, selected from the group consisting of: SEQ ID NOs: 3-4-5-8-9-10 and 14-15-16-19-20-21; and administering a therapeutically effective amount of a vascular endothelial growth factor (VEGF) antagonist, to the subject.

44. The method of claim 43, wherein the antibody or antigen-binding fragment comprises a HCVR/LCVR amino acid sequence pair selected from the group consisting of: SEQ ID NOs: 2/7 and 13/18.

45. The method of claim 43, wherein the VEGF antagonist comprises a VEGF receptor-based chimeric molecule (VEGF Trap).

46. The method of claim 45, wherein the VEGF Trap is aflibercept.

* * * * *

UNITED STATES PATENT AND TRADEMARK OFFICE
CERTIFICATE OF CORRECTION

PATENT NO. : 11,104,730 B2  
APPLICATION NO. : 15/972053  
DATED : August 31, 2021  
INVENTOR(S) : Jingtai Cao et al.

Page 1 of 1

It is certified that error appears in the above-identified patent and that said Letters Patent is hereby corrected as shown below:

On the Title Page

Item (73) Assignee:
"Regeneren Pharmaceuticals, Inc."
Should read:
--Regeneron Pharmaceuticals, Inc.--

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 23

<210> SEQ ID NO 1
<211> LENGTH: 384
<212> TYPE: DNA
<213> ORGANISM: Artificial Sequence
<220> FEATURE:
<223> OTHER INFORMATION: synthetic

<400> SEQUENCE: 1
gaggtacaac tggtggagtc tgggggaggc ttggcccagc cggggggtc cctgagactc      60 tcctgtgcag cctctggttt cactttcagt aactattgga tgagctgggt ccgccaggct     120
ccagggaagg ggctggagtg ggtggccaat ataaaacaag atgggagtga aaatactat      180 ttggagtctg tgaagggccg attcaccatc tccagagaca acgccaagaa tttattgtat     240
ctgcaaatga acagcctgag agccgaggac acggctgttt tttactgtgc gagacctgga     300
ctattacgct ttttggagcc tggaggcgc tactactccg gtatgaacgt ctggggccaa      360
gggaccacgg tcaccgtctc ctca                                            384

<210> SEQ ID NO 2
<211> LENGTH: 128
<212> TYPE: PRT
<213> ORGANISM: Artificial Sequence
<220> FEATURE:
<223> OTHER INFORMATION: synthetic

<400> SEQUENCE: 2

Glu Val Gln Leu Val Glu Ser Gly Gly Leu Ala Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Leu Glu Ser Val
    50                  55                  60

Lys Gly Arg Phe Thr Ile Ser Arg Asp Asn Ala Lys Asn Leu Leu Tyr
65                  70                  75                  80

Leu Gln Met Asn Ser Leu Arg Ala Glu Asp Thr Ala Val Phe Tyr Cys
                85                  90                  95

Ala Arg Pro Gly Leu Leu Arg Phe Leu Glu Pro Gly Arg Arg Tyr Tyr
            100                 105                 110

Ser Gly Met Asn Val Trp Gly Gln Gly Thr Thr Val Thr Val Ser Ser
        115                 120                 125

<210> SEQ ID NO 3
<211> LENGTH: 8
<212> TYPE: PRT
```

```
<213> ORGANISM: Artificial Sequence
<220> FEATURE:
<223> OTHER INFORMATION: synthetic

<400> SEQUENCE: 3

Gly Phe Thr Phe Ser Asn Tyr Trp
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Ile Lys Gln Asp Gly Ser Glu Lys
1               5

<210> SEQ ID NO 5
<211> LENGTH: 21
<212> TYPE: PRT
<213> ORGANISM: Artificial Sequence
<220> FEATURE:
<223> OTHER INFORMATION: synthetic

<400> SEQUENCE: 5

Ala Arg Pro Gly Leu Leu Arg Phe Leu Glu Pro Gly Arg Arg Tyr Tyr
1               5                   10                  15

Ser Gly Met Asn Val
            20

<210> SEQ ID NO 6
<211> LENGTH: 321
<212> TYPE: DNA
<213> ORGANISM: Artificial Sequence
<220> FEATURE:
<223> OTHER INFORMATION: synthetic

<400> SEQUENCE: 6
gacatccagt tgacccagtc tccatccttc ctgtctgcat ctgtaggaga cagagtcacc    60
atcacttgct gggccagtca gggcattcgc agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag tttaatagtt acccgtggac gttcggccaa   300
gggaccaagg tggaaatcaa a                                             321

<210> SEQ ID NO 7
<211> LENGTH: 107
<212> TYPE: PRT
<213> ORGANISM: Artificial sequence
<220> FEATURE:
<223> OTHER INFORMATION: synthetic

<400> SEQUENCE: 7

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Arg Ser Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Trp
                 85                  90                  95

Thr Phe Gly Gln Gly Thr Lys Val Glu Ile Lys
            100                 105
```

<210> SEQ ID NO 8
<211> LENGTH: 6
<212> TYPE: PRT
<213> ORGANISM: Artificial Sequence
<220> FEATURE:
<223> OTHER INFORMATION: synthetic

<400> SEQUENCE: 8

```
Gln Gly Ile Arg Ser Tyr
 1               5
```

<210> SEQ ID NO 9
<211> LENGTH: 3
<212> TYPE: PRT
<213> ORGANISM: Artificial Sequence
<220> FEATURE:
<223> OTHER INFORMATION: synthetic

<400> SEQUENCE: 9

```
Ala Ala Ser
 1
```

<210> SEQ ID NO 10
<211> LENGTH: 9
<212> TYPE: PRT
<213> ORGANISM: Artificial Sequence
<220> FEATURE:
<223> OTHER INFORMATION: synthetic

<400> SEQUENCE: 10

```
Gln Gln Phe Asn Ser Tyr Pro Trp Thr
 1               5
```

<210> SEQ ID NO 11
<211> LENGTH: 27
<212> TYPE: DNA
<213> ORGANISM: Artificial Sequence
<220> FEATURE:
<223> OTHER INFORMATION: synthetic

<400> SEQUENCE: 11
ctacagcata agagttaccc tcggacg                                         27

<210> SEQ ID NO 12
<211> LENGTH: 378
<212> TYPE: DNA
<213> ORGANISM: Artificial sequence
<220> FEATURE:
<223> OTHER INFORMATION: synthetic

<400> SEQUENCE: 12
caggtgaagt tggtggagtc tgggggaggc gtggtccagc ctgggaggtc cctgagactc    60
tcctgtgcag cgtctggatt caccttcagt aactatgtca tacactgggt ccgccaggct   120
ccaggcaagg ggctggagtg ggtggcggtt atatggtatg atggaagtaa taaatactat   180

```
gcagactccg tgaagggccg attcaccatc tccagagaca actccaagaa tacgctgtat    240
ttgcaaatga acagcctgag agccgaggac acggctgtgt attactgtgc gagagatcgg    300
gtggttcggg gagtcgatta ctactactac tacggtttgg acgtctgggg ccaagggacc    360
tcggtcaccg tctcctca                                                  378
```

```
<210> SEQ ID NO 13
<211> LENGTH: 126
<212> TYPE: PRT
<213> ORGANISM: Artificial Sequence
<220> FEATURE:
<223> OTHER INFORMATION: synthetic

<400> SEQUENCE: 13
```

```
Gln Val Lys Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Val Ile His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Val Arg Gly Val Asp Tyr Tyr Tyr Tyr Tyr Gly
            100                 105                 110

Leu Asp Val Trp Gly Gln Gly Thr Ser Val Thr Val Ser Ser
        115                 120                 125
```

```
<210> SEQ ID NO 14
<211> LENGTH: 8
<212> TYPE: PRT
<213> ORGANISM: Artificial Sequence
<220> FEATURE:
<223> OTHER INFORMATION: synthetic

<400> SEQUENCE: 14
```

```
Gly Phe Thr Phe Ser Asn Tyr Val
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: synthetic

<400> SEQUENCE: 15
```

```
Ile Trp Tyr Asp Gly Ser Asn Lys
1               5
```

```
<210> SEQ ID NO 16
<211> LENGTH: 19
<212> TYPE: PRT
<213> ORGANISM: Artificial Sequence
<220> FEATURE:
<223> OTHER INFORMATION: synthetic

<400> SEQUENCE: 16
```

```
Ala Arg Asp Arg Val Val Arg Gly Val Asp Tyr Tyr Tyr Tyr Tyr Gly
```

```
1               5                   10                  15
Leu Asp Val

<210> SEQ ID NO 17
<211> LENGTH: 321
<212> TYPE: DNA
<213> ORGANISM: Artificial Sequence
<220> FEATURE:
<223> OTHER INFORMATION: synthetic

<400> SEQUENCE: 17
gaaatagtga tgacgcagtc tccagccacc ctgtctgtgt ctccagggga aagagccacc    60
ctctcctgca gggccagtca gagtgttaga agcaacttag cctggtacca acagaaacct   120
ggccaggctc ccaggctcct catctatggt gcatcctcca gggccactgg tatcccagcc   180
aggttcagtg gcactgggtc tgggacagag ttcactctca ccatcagcag cctgcagtct   240
gacgattttg cagtttatta ctgtcagcaa tataataagt ggcctcggac gttcggccaa   300
gggaccaagg tggaaatcaa g                                             321

<210> SEQ ID NO 18
<211> LENGTH: 107
<212> TYPE: PRT
<213> ORGANISM: Artificial Sequence
<220> FEATURE:
<223> OTHER INFORMATION: synthetic

<400> SEQUENCE: 18
```

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Ala Arg Phe Ser Gly
    50                  55                  60

Thr Gly Ser Gly Thr Glu Phe Thr Leu Thr Ile Ser Ser Leu Gln Ser
65                  70                  75                  80

Asp Asp Phe Ala Val Tyr Tyr Cys Gln Gln Tyr Asn Lys Trp Pro Arg
                85                  90                  95

Thr Phe Gly Gln Gly Thr Lys Val Glu Ile Lys
            100                 105

```
<210> SEQ ID NO 19
<211> LENGTH: 6
<212> TYPE: PRT
<213> ORGANISM: Artificial Sequence
<220> FEATURE:
<223> OTHER INFORMATION: synthetic

<400> SEQUENCE: 19
```

Gln Ser Val Arg Ser Asn
1               5

```
<210> SEQ ID NO 20
<211> LENGTH: 3
<212> TYPE: PRT
<213> ORGANISM: Artificial sequence
<220> FEATURE:
<223> OTHER INFORMATION: synthetic

<400> SEQUENCE: 20
```

```
Gly Ala Ser
  1

<210> SEQ ID NO 21
<211> LENGTH: 9
<212> TYPE: PRT
<213> ORGANISM: Artificial Sequence
<220> FEATURE:
<223> OTHER INFORMATION: synthetic

<400> SEQUENCE: 21

Gln Gln Tyr Asn Lys Trp Pro Arg Thr
  1               5

<210> SEQ ID NO 22
<211> LENGTH: 380
<212> TYPE: PRT
<213> ORGANISM: Artificial Sequence
<220> FEATURE:
<223> OTHER INFORMATION: synthetic

<400> SEQUENCE: 22

Met Glu Glu Gly Gly Asp Phe Asp Asn Tyr Tyr Gly Ala Asp Asn Gln
  1               5                  10                  15

Ser Glu Cys Glu Tyr Thr Asp Trp Lys Ser Ser Gly Ala Leu Ile Pro
                 20                  25                  30

Ala Ile Tyr Met Leu Val Phe Leu Gly Thr Thr Gly Asn Gly Leu
                 35                  40                  45

Val Leu Trp Thr Val Phe Arg Ser Ser Arg Glu Lys Arg Arg Ser Ala
 50                  55                  60

Asp Ile Phe Ile Ala Ser Leu Ala Val Ala Asp Leu Thr Phe Val Val
 65                  70                  75                  80

Thr Leu Pro Leu Trp Ala Thr Tyr Thr Tyr Arg Asp Tyr Asp Trp Pro
                 85                  90                  95

Phe Gly Thr Phe Phe Cys Lys Leu Ser Ser Tyr Leu Ile Phe Val Asn
                100                 105                 110

Met Tyr Ala Ser Val Phe Cys Leu Thr Gly Leu Ser Phe Asp Arg Tyr
                115                 120                 125

Leu Ala Ile Val Arg Pro Val Ala Asn Ala Arg Leu Arg Leu Arg Val
            130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
                180                 185                 190

Ser Glu Trp Ala Trp Glu Val Gly Leu Gly Val Ser Ser Thr Thr Val
            195                 200                 205

Gly Phe Val Val Pro Phe Thr Ile Met Leu Thr Cys Tyr Phe Phe Ile
        210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
                260                 265                 270

Leu Gly Ser Leu Leu His Trp Pro Cys Asp Phe Asp Leu Phe Leu Met
```

```
                       275                 280                 285
Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                    325                 330                 335

Ser Ser Ser Gly Glu Lys Ser Ala Ser Tyr Ser Ser Gly His Ser Gln
                340                 345                 350

Gly Pro Gly Pro Asn Met Gly Lys Gly Gly Glu Gln Met His Glu Lys
                    355                 360                 365

Ser Ile Pro Tyr Ser Gln Glu Thr Leu Val Val Asp
    370                 375                 380

<210> SEQ ID NO 23
<211> LENGTH: 458
<212> TYPE: PRT
<213> ORGANISM: Homo sapiens

<400> SEQUENCE: 23

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270
```

```
Val Val Val Asp Val Ser His Glu Asp Pro Glu Val Lys Phe Asn Trp
            275             280             285

Tyr Val Asp Gly Val Glu Val His Asn Ala Lys Thr Lys Pro Arg Glu
    290             295             300

Glu Gln Tyr Asn Ser Thr Tyr Arg Val Val Ser Val Leu Thr Val Leu
305             310             315             320

His Gln Asp Trp Leu Asn Gly Lys Glu Tyr Lys Cys Lys Val Ser Asn
                325             330             335

Lys Ala Leu Pro Ala Pro Ile Glu Lys Thr Ile Ser Lys Ala Lys Gly
                340             345             350

Gln Pro Arg Glu Pro Gln Val Tyr Thr Leu Pro Pro Ser Arg Asp Glu
            355             360             365

Leu Thr Lys Asn Gln Val Ser Leu Thr Cys Leu Val Lys Gly Phe Tyr
        370             375             380

Pro Ser Asp Ile Ala Val Glu Trp Glu Ser Asn Gly Gln Pro Glu Asn
385             390             395             400

Asn Tyr Lys Thr Thr Pro Pro Val Leu Asp Ser Asp Gly Ser Phe Phe
                405             410             415

Leu Tyr Ser Lys Leu Thr Val Asp Lys Ser Arg Trp Gln Gln Gly Asn
            420             425             430

Val Phe Ser Cys Ser Val Met His Glu Ala Leu His Asn His Tyr Thr
            435             440             445

Gln Lys Ser Leu Ser Leu Ser Pro Gly Lys
450             455
```